(12) United States Patent
Tebbe et al.

(10) Patent No.: US 10,709,470 B2
(45) Date of Patent: Jul. 14, 2020

(54) FEATURES TO COUPLE ACOUSTIC DRIVETRAIN COMPONENTS IN ULTRASONIC SURGICAL INSTRUMENT

(71) Applicant: ETHICON LLC, Guaynabo, PR (US)

(72) Inventors: Mark E. Tebbe, Lebanon, OH (US); Ion V. Nicolaescu, Carpentersville, IL (US); Tony C. Siebel, Cincinnati, OH (US); Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 283 days.

(21) Appl. No.: 15/644,944

(22) Filed: Jul. 10, 2017

(65) Prior Publication Data
US 2019/0008547 A1 Jan. 10, 2019

(51) Int. Cl.
*A61B 17/32* (2006.01)
*A61B 17/00* (2006.01)
(Continued)

(52) U.S. Cl.
CPC .......... *A61B 17/320092* (2013.01); *A61B 2017/0046* (2013.01); *A61B 2017/00407* (2013.01); *A61B 2017/00473* (2013.01); *A61B 2017/00477* (2013.01); *A61B 2017/2929* (2013.01); *A61B 2017/320071* (2017.08);
(Continued)

(58) Field of Classification Search
CPC . A61B 17/320068; A61B 17/320016–320036; A61B 17/068–076; A61B 17/32–326; A61B 2017/320069–320098; A61B 2017/320024–32004; A61B 2017/0688–07285; A61B 2017/320004–3225
See application file for complete search history.

(56) References Cited

U.S. PATENT DOCUMENTS 5,059,210 A * 10/1991 Clark ................. A61B 17/3215
606/169
5,322,055 A 6/1994 Davison et al.
(Continued)

OTHER PUBLICATIONS

U.S. Appl. No. 15/644,930, filed Jul. 10, 2017.

*Primary Examiner* — George J Ulsh
(74) *Attorney, Agent, or Firm* — Frost Brown Todd LLC

(57) ABSTRACT

An ultrasonic surgical instrument includes a body, an ultrasonic transducer rotatably supported within the body and having a threaded distal end, a shaft extending from the body, a waveguide extending through the shaft and having a threaded proximal end configured to threadedly engage the threaded distal end to define a threaded coupling, and an end effector at a distal end of the shaft. An integrated torque wrench mechanism is arranged within the body and includes a first torque wrench member rotationally coupled with a proximal end of the transducer, and a second torque wrench member arranged proximally of the first torque wrench member. The torque wrench members are configured to selectively couple together and frictionally engage one another to facilitate application of a predetermined maximum torque to the threaded coupling. The torque wrench members are configured to automatically decouple upon application of the predetermined maximum torque to the threaded coupling.

19 Claims, 21 Drawing Sheets

(51) Int. Cl.
*A61B 90/00* (2016.01)
*A61B 17/29* (2006.01)

(52) U.S. Cl.
CPC .............. *A61B 2017/320074* (2017.08); *A61B 2017/320094* (2017.08); *A61B 2017/320095* (2017.08); *A61B 2017/320098* (2017.08); *A61B 2090/031* (2016.02)

(56) References Cited

U.S. PATENT DOCUMENTS

| | | | |
|---|---|---|---|
| 5,792,135 | A | 8/1998 | Madhani et al. |
| 5,817,084 | A | 10/1998 | Jensen |
| 5,873,873 | A | 2/1999 | Smith et al. |
| 5,878,193 | A | 3/1999 | Wang et al. |
| 5,980,510 | A | 11/1999 | Tsonton et al. |
| 6,231,565 | B1 | 5/2001 | Tovey et al. |
| 6,283,981 | B1 | 9/2001 | Beaupre |
| 6,309,400 | B2 | 10/2001 | Beaupre |
| 6,325,811 | B1 | 12/2001 | Messerly |
| 6,364,888 | B1 | 4/2002 | Niemeyer et al. |
| 6,423,082 | B1 | 7/2002 | Houser et al. |
| 6,773,444 | B2 | 8/2004 | Messerly |
| 6,783,524 | B2 | 8/2004 | Anderson et al. |
| 7,524,320 | B2 | 4/2009 | Tierney et al. |
| 7,691,098 | B2 | 4/2010 | Wallace et al. |
| 7,806,891 | B2 | 10/2010 | Nowlin et al. |
| 8,057,498 | B2 | 11/2011 | Robertson |
| 8,461,744 | B2 | 6/2013 | Wiener et al. |
| 8,479,969 | B2 | 7/2013 | Shelton, IV |
| 8,497,436 | B2 | 7/2013 | Palmer et al. |
| 8,502,091 | B2 | 8/2013 | Palmer et al. |
| 8,573,461 | B2 | 11/2013 | Shelton, IV et al. |
| 8,573,465 | B2 | 11/2013 | Shelton, IV |
| 8,591,536 | B2 | 11/2013 | Robertson |
| 8,602,288 | B2 | 12/2013 | Shelton, IV et al. |
| 8,616,431 | B2 | 12/2013 | Timm et al. |
| 8,623,027 | B2 | 1/2014 | Price et al. |
| 8,663,220 | B2 | 3/2014 | Wiener et al. |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,017,355 | B2 | 4/2015 | Smith et al. |
| 9,050,125 | B2 * | 6/2015 | Boudreaux ........ A61B 18/1442 |
| 9,095,367 | B2 | 8/2015 | Olson et al. |
| 9,301,759 | B2 | 4/2016 | Spivey et al. |
| 9,750,521 | B2 | 9/2017 | Lamping et al. |
| 9,949,785 | B2 | 4/2018 | Price et al. |
| 2012/0116363 | A1 * | 5/2012 | Houser ................. A61B 34/25 606/1 |
| 2012/0116394 | A1 * | 5/2012 | Timm .................... A61B 34/25 606/45 |
| 2015/0148829 | A1 | 5/2015 | Kimball et al. |
| 2015/0245850 | A1 * | 9/2015 | Hibner ............... A61B 18/1482 606/171 |
| 2017/0000541 | A1 | 1/2017 | Yates et al. |

* cited by examiner

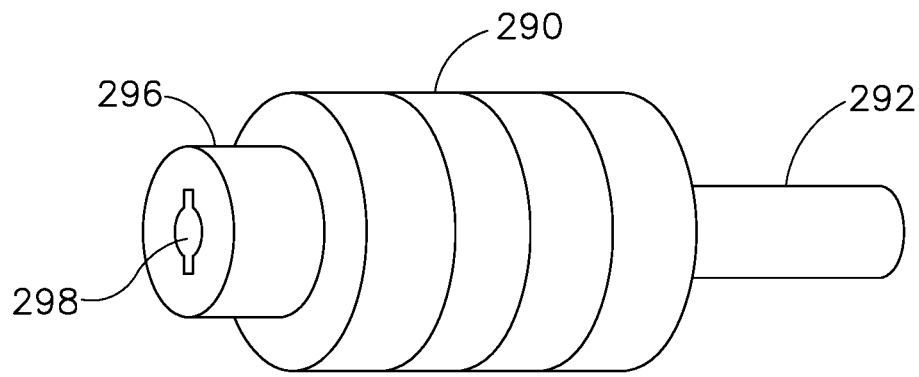
Fig.21
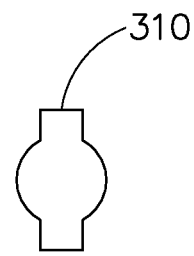 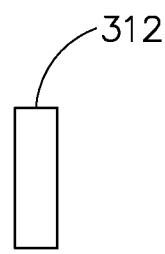 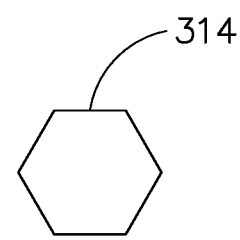
Fig.22A  Fig.22B  Fig.22C
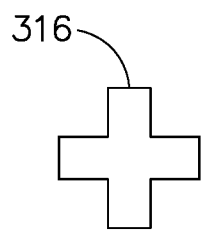 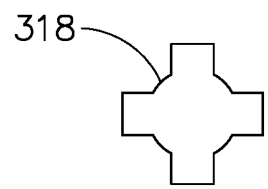
Fig.22D  Fig.22E

FEATURES TO COUPLE ACOUSTIC DRIVETRAIN COMPONENTS IN ULTRASONIC SURGICAL INSTRUMENT

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

An ultrasonic surgical instrument generally includes an ultrasonic transducer and an ultrasonic blade configured to be driven by the ultrasonic transducer. Various ultrasonic surgical instruments enable the ultrasonic blade to be selectively coupled with and decoupled from the ultrasonic transducer, via a threaded coupling between the two components. It is desirable to apply an appropriate amount of torque to this threaded coupling when assembling the blade with the transducer. Applying too much torque can cause the threaded coupling to fracture and fail during use, and applying too little torque can cause the threaded coupling to loosen and inhibit effective transmission of ultrasonic energy to tissue during use. Either result is undesirable, and can render the surgical instrument ineffective or entirely inoperable. Ultrasonic blades and transducers of conventional ultrasonic surgical instruments may be assembled with a hand-held torque wrench tool that is provided separately from the surgical instrument. The torque wrench tool includes features that limit application of additional torque to the threaded coupling between the ultrasonic blade and transducer once a predetermined amount of torque has been reached. An example of such a torque wrench tool is disclosed in U.S. Pat. No. 5,059,210, entitled "Apparatus and Methods for Attaching and Detaching an Ultrasonic Actuated Blade/Coupler and an Acoustical Mount Therefor," issued Oct. 22, 1991, the disclosure of which is incorporated by reference herein.

While various types of ultrasonic surgical instruments and torque wrench mechanisms have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 21 depicts a perspective view of the ultrasonic transducer of the ultrasonic surgical instrument of FIG. 20, showing the keyway formed in a proximal end of the ultrasonic transducer;

FIG. 22A depicts a first exemplary cross-sectional shape of the keyway and the key element of the ultrasonic transducer and the torque wrench device of FIG. 20;

FIG. 22B depicts a second exemplary cross-sectional shape of the keyway and the key element of the ultrasonic transducer and the torque wrench device of FIG. 20;

FIG. 22C depicts a third exemplary cross-sectional shape of the keyway and the key element of the ultrasonic transducer and the torque wrench device of FIG. 20;

FIG. 22D depicts a fourth exemplary cross-sectional shape of the keyway and the key element of the ultrasonic transducer and the torque wrench device of FIG. 20; and FIG. 22E depicts a fifth exemplary cross-sectional shape of the keyway and the key element of the ultrasonic transducer and the torque wrench device of FIG. 20.

Figure 1:
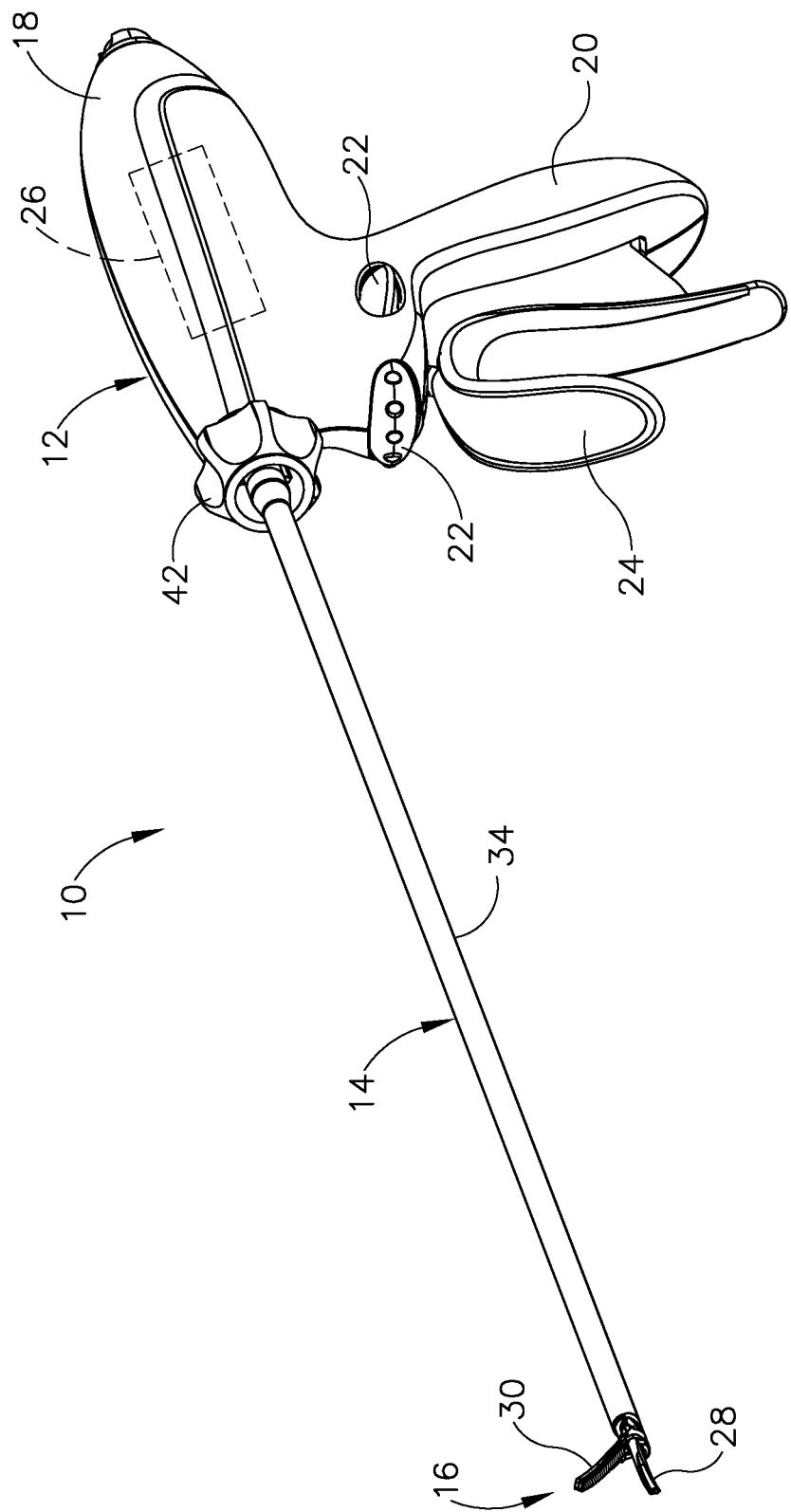
FIG. 1 depicts a perspective view of an exemplary ultrasonic surgical instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. EXEMPLARY ULTRASONIC SURGICAL INSTRUMENT HAVING INTEGRATED TORQUE WRENCH MECHANISM

A. Overview of Exemplary Ultrasonic Surgical Instrument

Figure 2:
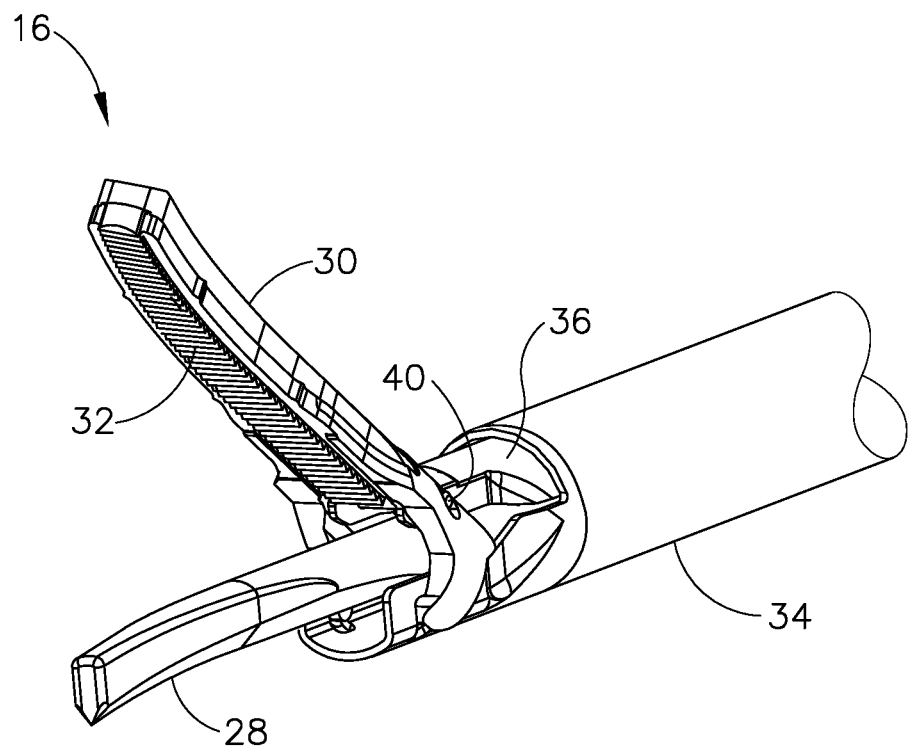
FIG. 2 depicts a perspective view of an end effector of the ultrasonic surgical instrument of FIG. 1.

FIGS. 1 and 2 show an exemplary ultrasonic surgical instrument (10) that includes a handle assembly (12), a shaft assembly (14) extending distally from handle assembly (12), and an end effector (16) arranged at a distal end of shaft assembly (14). Handle assembly (12) comprises a body (18) including a pistol grip (20) and energy control buttons (22) configured to be manipulated by a surgeon to control various aspects of tissue treatment energy delivered by surgical instrument (10). A trigger (24) is coupled to a lower portion of body (18) and is pivotable toward and away from pistol grip (20) to selectively actuate end effector (16). In other suitable variations of surgical instrument (10), handle assembly (12) may comprise a scissor grip configuration, for example. Body (18) houses an ultrasonic transducer (26), shown schematically in FIG. 1, configured to deliver ultrasonic energy to end effector (16), as described in greater detail below.

As shown best in FIG. 2, end effector (16) includes an ultrasonic blade (28) and a clamp arm (30) configured to selectively pivot toward and away from ultrasonic blade (28), for clamping tissue therebetween. Clamp arm (30) includes a clamp pad (32) arranged on a clamping side thereof. Ultrasonic blade (28) is acoustically coupled with ultrasonic transducer (26), which is configured to drive (i.e., vibrate) ultrasonic blade (28) at ultrasonic frequencies for cutting and/or sealing tissue positioned in contact with ultrasonic blade (28). Clamp arm (30) is operatively coupled with trigger (24) such that clamp arm (30) is configured to pivot toward ultrasonic blade (28), to a closed position (not shown), in response to pivoting of trigger (24) toward pistol grip (20). Further, clamp arm (30) is configured to pivot away from ultrasonic blade (28), to an open position, shown in FIGS. 1 and 2, in response to pivoting of trigger (24) away from pistol grip (20). Various suitable ways in which clamp arm (30) may be coupled with trigger (24) will be apparent to those of ordinary skill in the art in view of the teachings provided herein. In some versions, one or more resilient members may be incorporated to bias clamp arm (30) and/or trigger (24) toward the open position.

Shaft assembly (14) of the present example extends along a longitudinal axis and includes an outer tube (34), an inner tube (36) received within outer tube (34), and an ultrasonic waveguide (38) (see FIG. 3A) supported within and extending longitudinally through inner tube (36). Ultrasonic blade (28) is formed integrally with and extends distally from waveguide (38). As shown in FIG. 2, a proximal end of clamp arm (30) is pivotally coupled to distal ends of outer and inner tubes (34, 36), enabling clamp arm (30) to pivot relative to shaft assembly (14) about a pivot axis defined by a pivot pin (40) extending transversely through the distal end of inner tube (36).

In the present example, inner tube (36) is longitudinally fixed relative to handle assembly (18), and outer tube (34) is configured to translate relative to inner tube (36) and handle assembly (18), along the longitudinal axis of shaft assembly (20). As outer tube (34) translates distally, clamp arm (30) pivots about its pivot axis toward its open position. As outer tube (34) translates proximally, clamp arm (30) pivots about its pivot axis in an opposite direction toward its closed position. Though not shown, a proximal end of outer tube (34) is operatively coupled with trigger (24) such that actuation of trigger (24) causes translation of outer tube (34) relative to inner tube (36), thereby opening or closing clamp arm (30). In other suitable configurations not shown herein, outer tube (34) may be longitudinally fixed and inner tube (36) may be configured to translate for moving clamp arm (30) between its open and closed positions. Various other suitable mechanisms for actuating clamp arm (30) between its open and closed positions will be apparent to those of ordinary skill in the art.

Figure 3A:
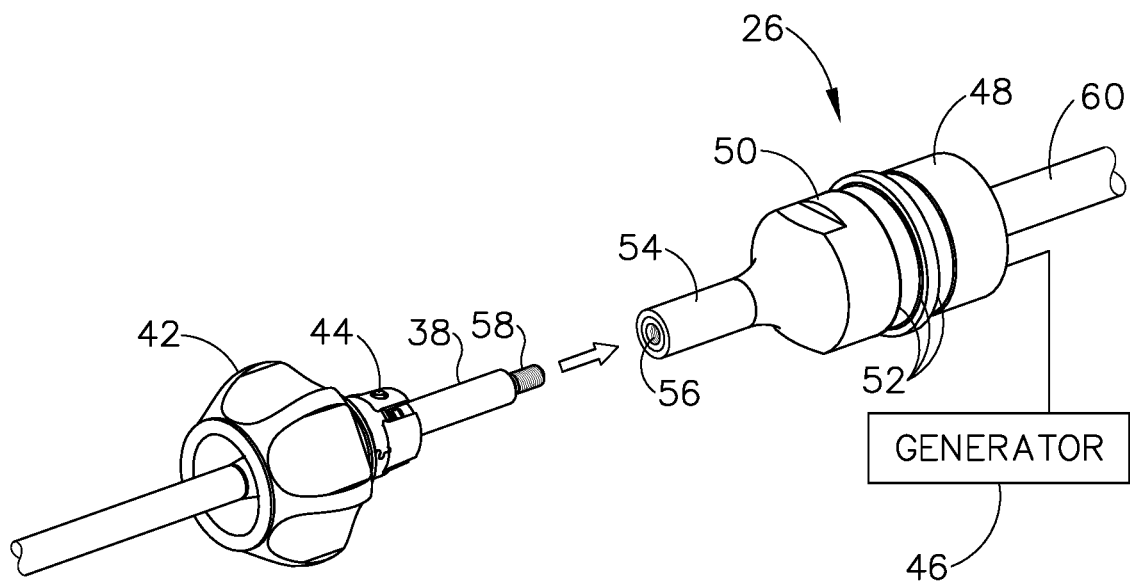
FIG. 3A depicts a schematic perspective view of an ultrasonic transducer, a waveguide, and a rotation knob of the ultrasonic surgical instrument of FIG. 1, with an outer tube and an inner tube thereof being omitted, showing attachment of the waveguide to the ultrasonic transducer.

Shaft assembly (14) and end effector (16) are configured to rotate together relative to body (18) about the longitudinal axis defined by shaft assembly (14). As shown in FIGS. 1 and 3A, shaft assembly (14) further includes a rotation knob (42) arranged at a proximal end thereof. Rotation knob (42) is rotatably coupled to body (18) of handle assembly (12), and is rotationally fixed to outer tube (34), inner tube (36), and waveguide (38) by a coupling pin (44) extending transversely therethrough. Coupling pin (44) is arranged at a longitudinal location corresponding to an acoustic node of waveguide (38). In other examples, rotation knob (42) may be rotationally fixed to the remaining components of shaft assembly (14) in various other manners, for example as disclosed in U.S. patent application Ser. No. 15/644,930, entitled "Acoustic Drivetrain with External Collar at Nodal Position," filed on Jul. 10, 2017, published as U.S. Pub. No. 2019/0008546 on Jan. 10, 2019, the disclosure of which is incorporated by reference herein. Rotation knob (42) is configured to be gripped by a user to selectively manipulate the rotational orientation of shaft assembly (14) and end effector (16) relative to handle assembly (12).

Figure 3B:
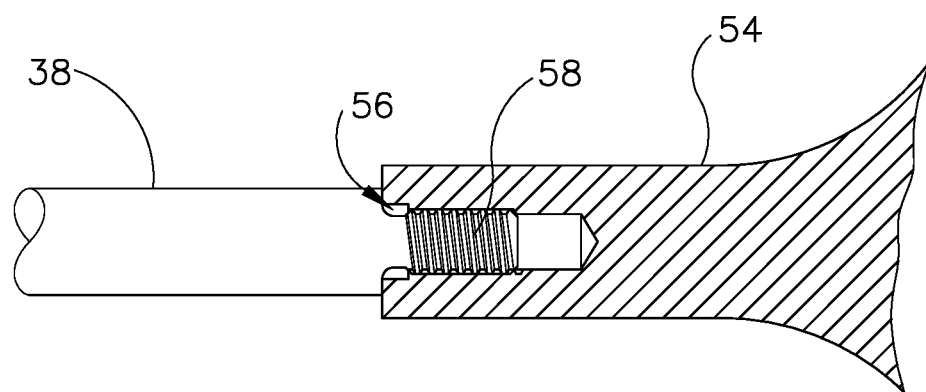
FIG. 3B depicts a side sectional view of a threaded coupling between the ultrasonic transducer and the waveguide of FIG. 3A.

FIGS. 3A and 3B show additional details of ultrasonic transducer (26) and waveguide (38). In particular, ultrasonic transducer (26) and waveguide (38) are configured to threadedly couple together. Accordingly, waveguide (38) is configured to acoustically couple ultrasonic transducer (26) with ultrasonic blade (28), and thereby communicate ultrasonic mechanical vibrations from transducer (26) to blade (28). In this manner, ultrasonic transducer (26), waveguide (38), and ultrasonic blade (28) together define an acoustic assembly of ultrasonic surgical instrument (10). Ultrasonic transducer (26) is rotatably supported within body (18) of handle assembly (12), and is configured to rotate with shaft assembly (14), including waveguide (38), and end effector (16) about the longitudinal axis of shaft assembly (14).

As shown schematically in FIG. 3A, ultrasonic transducer (26) is electrically coupled with a generator (46), which may be provided externally of ultrasonic surgical instrument (10) or integrated within surgical instrument (10). During use, generator (46) powers ultrasonic transducer (26) to produce ultrasonic mechanical vibrations, which are communicated distally through waveguide (38) to ultrasonic blade (28). Ultrasonic blade (28) is caused to oscillate longitudinally in the range of approximately 10 to 500 microns peak-to-peak, for example, and in some instances in the range of approximately 20 to 200 microns, at a predetermined vibratory frequency $f_o$ of approximately 50 kHz, for example. Vibrating ultrasonic blade (28) may be positioned in direct contact with tissue, with or without assistive clamping force provided by clamp arm (30), to impart ultrasonic vibrational energy to the tissue and thereby cut and/or seal the tissue. For example, blade (28) may cut through tissue clamped between clamp arm (30) and a clamping side of blade (28), or blade (28) may cut through tissue positioned in contact with an oppositely disposed non-clamping side of blade (28) having an edge, for example during a "back-cutting" movement. In some versions, waveguide (38) may be configured to amplify the ultrasonic vibrations delivered to blade (28). Waveguide (38) may include various features operable to control the gain of the vibrations, and/or features suitable to tune waveguide (38) to a selected resonant frequency.

In the present example, ultrasonic transducer (26) includes a first resonator (or "end-bell") (48), a conically shaped second resonator (or "fore-bell") (50), and a transduction portion arranged between end-bell (48) and fore-bell (50) and comprising a plurality of piezoelectric elements (52). A compression bolt (not shown) extends distally, coaxially through end-bell (48) and piezoelectric elements (52), and is threadedly received within a proximal end of fore-bell (50). A velocity transformer (or "horn") (54) extends distally from fore-bell (146) and includes an internally threaded bore (56) configured to receive and threadedly couple with an externally threaded proximal tip (58) of waveguide (38). A shaft-like transducer coupling member (60) extends proximally from end-bell (48) and is configured to cooperate with a user-engageable member coupled to body (18) of handle assembly (12) to define a torque wrench mechanism integrated within ultrasonic surgical instrument (10). As described in greater detail below, the integrated torque wrench mechanism is configured to facilitate application of an optimal amount of torque to the threaded coupling between waveguide (38) and ultrasonic transducer (26) during assembly of ultrasonic surgical instrument (10), thereby ensuring a proper threaded connection between the two components and protecting against over and under tightening.

Figure 4:
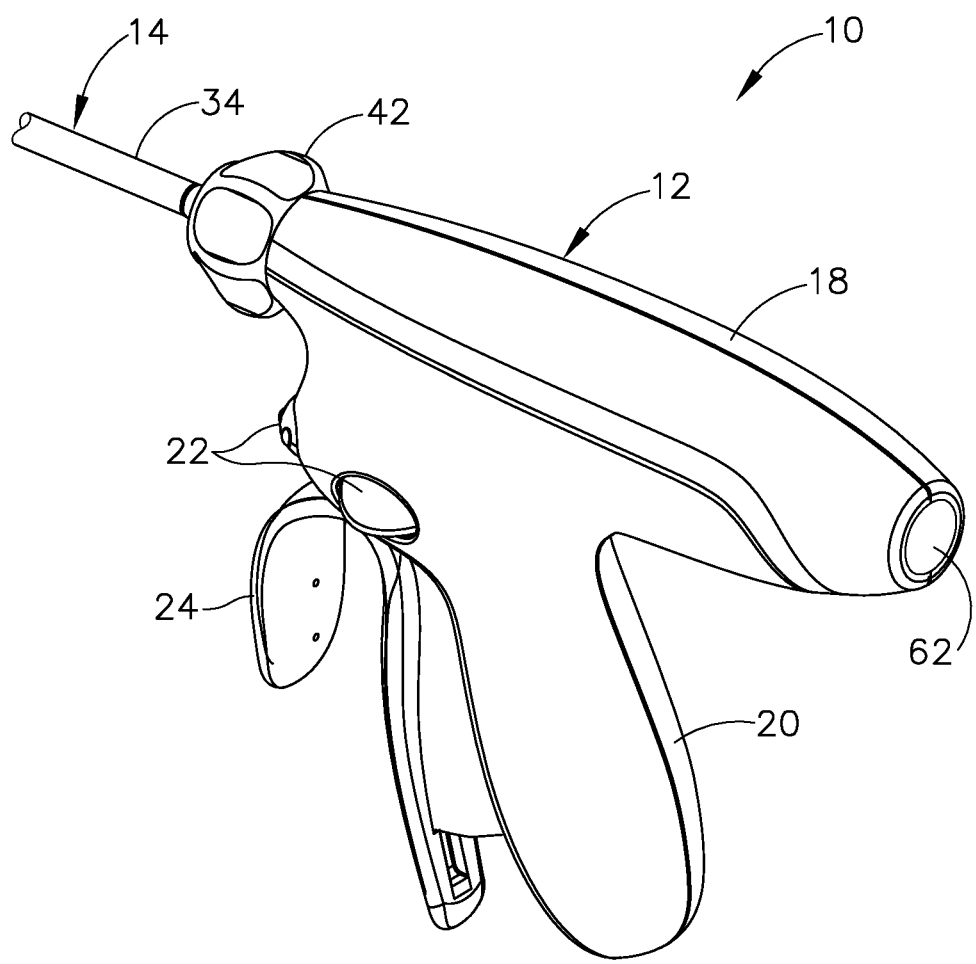
FIG. 4 depicts a rear perspective view of the ultrasonic surgical instrument of FIG. 1.
Figure 5:
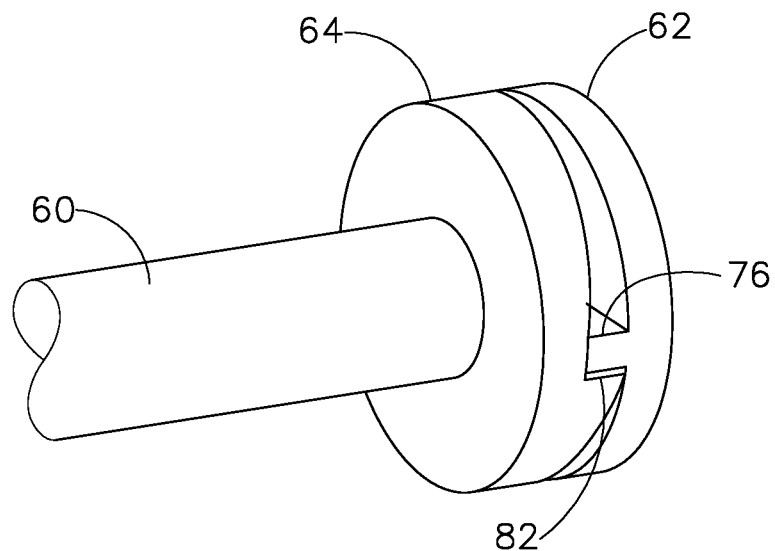
FIG. 5 depicts a perspective view of an integrated torque wrench mechanism of the ultrasonic surgical instrument of FIG. 4.
Figure 6:
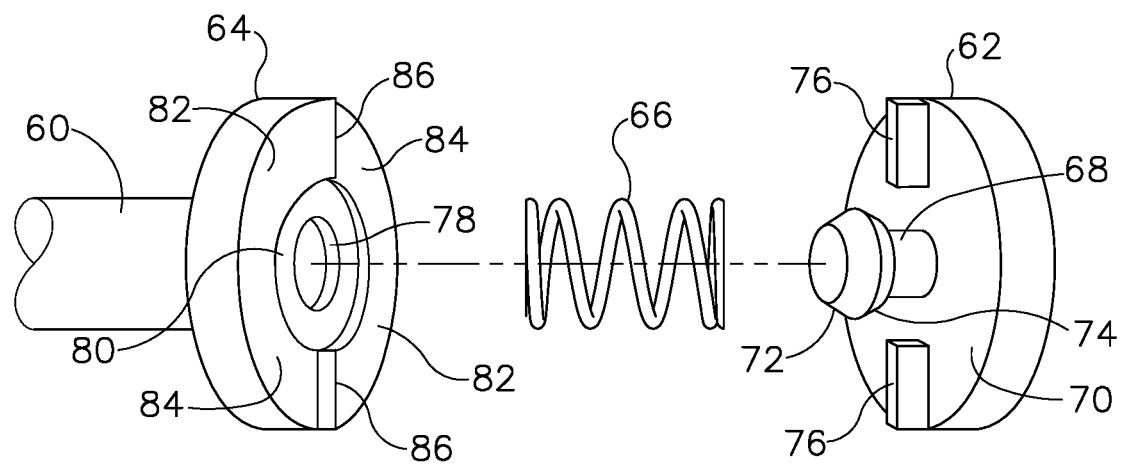
FIG. 6 depicts a disassembled perspective view of the integrated torque wrench mechanism of FIG. 5, showing first and second wrench members thereof.

B. Integrated Torque Wrench Mechanism Having Proximal and Distal Torque Wrench Members FIGS. 4-6 show details of an exemplary torque wrench mechanism integrated within a proximal end portion of ultrasonic surgical instrument (10). The torque wrench mechanism of the present example includes a proximal wrench member (62), a distal wrench member (64) configured to mate with proximal wrench member (62), and a compression spring (66) arranged therebetween. Proximal wrench member (62) is in the form of a disk-like structure coupled to a proximal end of body (18) of handle assembly (12), and distal wrench member (64) is in the form of a disk-like structure that defines, or is otherwise affixed to, a proximal end of transducer coupling member (60). In the present example, proximal wrench member (62) is configured to translate proximally and distally relative to body (18) and distal wrench member (64), and is rotationally fixed relative to body (18). Distal wrench member (64) is configured to rotate relative to body (18) with ultrasonic transducer (26) and is generally fixed longitudinally. Compression spring (66) is configured to resiliently bias proximal wrench member (62) proximally, away from distal wrench member (64). As shown in FIG. 4, a proximal portion of proximal wrench member (62) is exposed through an opening formed in a proximal end of body (18) of handle assembly (12), and is configured to be engaged by a user to activate the torque wrench features of the torque wrench mechanism, as described below.

As shown in FIG. 6, proximal wrench member (62) includes a post (68) projecting distally from a distal face (70) thereof along the longitudinal axis of surgical instrument (10). Post (68) includes a distally tapering head (72) having a proximally tapering shoulder surface (74). Proximal wrench member (62) further includes a pair of tabs (76) projecting distally from distal face (70). In the present example, tabs (76) are arranged at diametrically opposed positions and are spaced radially outwardly from post (68) at an outer circumference of proximal wrench member (62). As described below, tabs (76) are configured to function as cam follower elements.

Distal wrench member (64) includes an opening (78) extending distally through a proximal face (80) thereof along the longitudinal axis of surgical instrument (10), and a pair of cam ramps (82) extending circumferentially about opening (78) at an outer circumference of distal wrench member (64). Each cam ramp (82) includes a ramp base (84)

and a ramp peak (86) that is elevated proximally beyond the respective ramp base (84). Each ramp base (84) may lie substantially flush with proximal face (80). In the present example, each cam ramp (82) extends from its ramp base (84) to its ramp peak (86) along a circumferential path passing through a 180-degree half of proximal face (80). Consequently, as shown in FIG. 6, ramp peaks (86) and ramp bases (84) are diametrically opposed from one another along the same plane. Other versions of ultrasonic surgical instrument (10) may include various other suitable arrangements and/or quantities of post (68), opening (78), tabs (76), and cam ramps (82). For example, each cam ramp (82) may extend circumferentially about only a 90-degree section of proximal face (80). In another example, post (68) and tabs (76) may be arranged on distal wrench member (64), and cam ramps (82) and opening (78) may arranged on proximal wrench member (62). As described in greater detail below with reference to FIGS. 7A-7D, opening (78) is configured to releasably retain post (68) in a snap-fit engagement, and cam ramps (82) are configured to frictionally engage tabs (76) to facilitate and control application of torque to the threaded coupling between ultrasonic transducer (26) and waveguide (38).

Figure 7A:
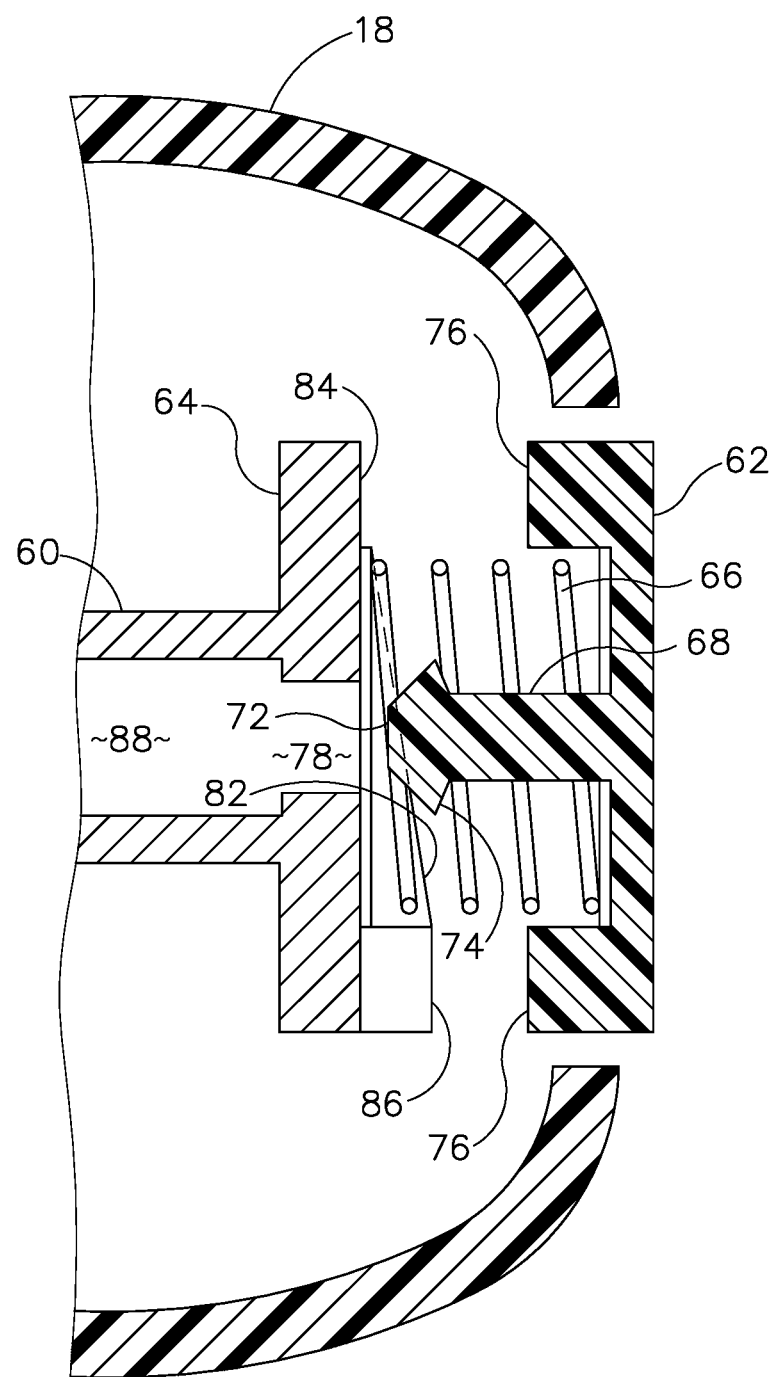
FIG. 7A depicts a schematic side sectional view of a proximal portion of a handle assembly of the ultrasonic surgical instrument of FIG. 4, showing the first wrench member of the integrated torque wrench mechanism in a proximal position relative to the second wrench member.

C. Exemplary Method for Threadedly Coupling Waveguide with Ultrasonic Transducer Using Integrated Torque Wrench Mechanism FIGS. 7A-7D show an exemplary method of threadedly coupling waveguide (38) to ultrasonic transducer (26) using integrated torque wrench members (62, 64) described above to facilitate application of a predetermined maximum torque to the threaded coupling. FIG. 7A shows proximal wrench member (62) arranged in a proximal position in which it is decoupled from distal wrench member (64). As shown, compression spring (66) is arranged along the longitudinal axis of surgical instrument (10) such that a proximal spring end confronts distal face (70) of proximal wrench member (62), a distal spring end confronts proximal face (80) of distal wrench member (64), and post (68) extends distally through spring (66) and in axial alignment with opening (78).

Figure 7B:
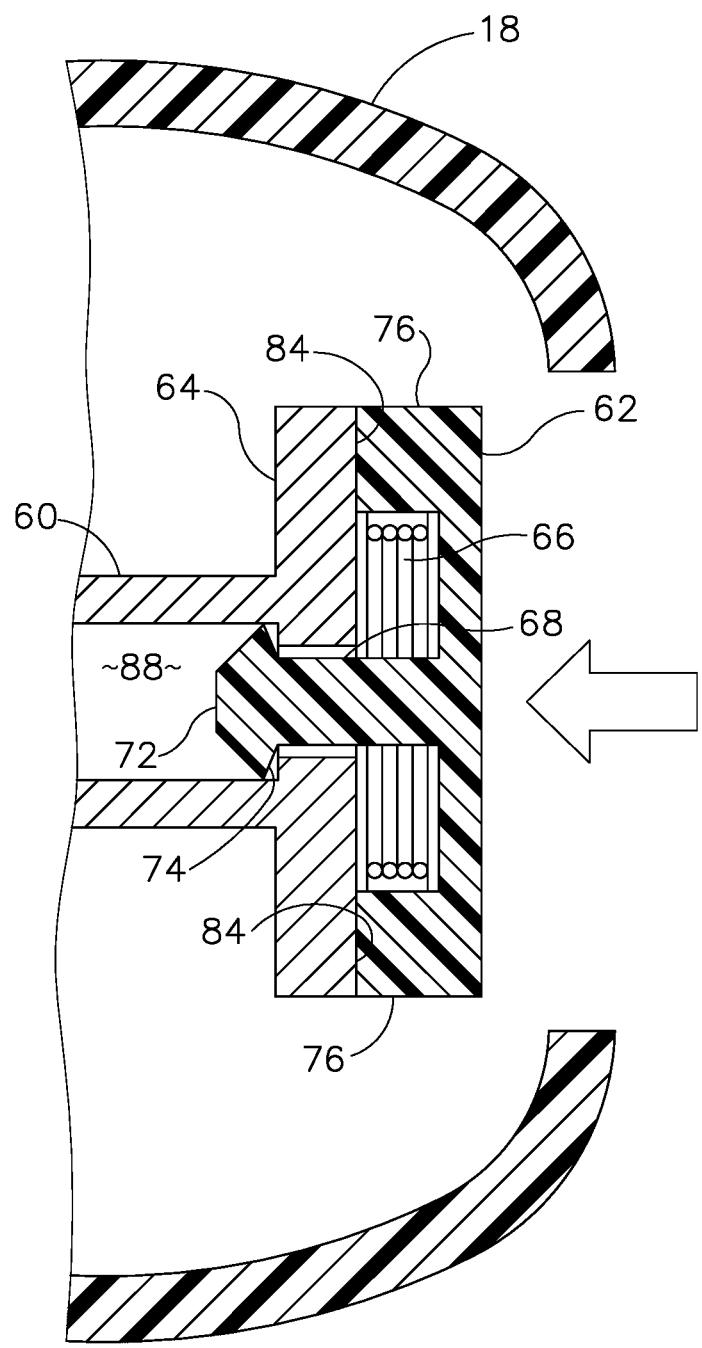
FIG. 7B depicts a schematic side sectional view of the proximal portion of the handle assembly of FIG. 7A, showing the first wrench member of the integrated torque wrench mechanism in a distal position in which the first wrench member releasably couples with the second wrench member.

FIG. 7B shows proximal wrench member (62) in a distal position in which post (68) is received within opening (78) of distal wrench member (64) to form a releasable snap-fit connection, and tabs (76) of proximal wrench member (62) frictionally engage cam ramp bases (84) of distal wrench member (64). In the present example, opening (78) is formed with a slightly smaller diameter than head (72) and opens distally to an internal bore (88) of a larger diameter, thereby enabling head (72) to engage distal wrench member (64) in a snap-fit engagement. As shown, placing proximal wrench member (62) in its distal position includes compressing compression spring (66) between wrench members (62, 64), such that proximal wrench member (62) remains biased proximally. It will be understood, however, that the axial extension force required for overcoming the snap-fit engagement of wrench members (62, 64) is greater than the axial extension force exerted by compression spring (66) in its compressed state. Accordingly, spring (66) does not operate to decouple wrench members (62, 64) from one another, but rather only to bias proximal wrench member (62) proximally once wrench members (62, 64) have been decoupled, as described below.

Figure 7C:
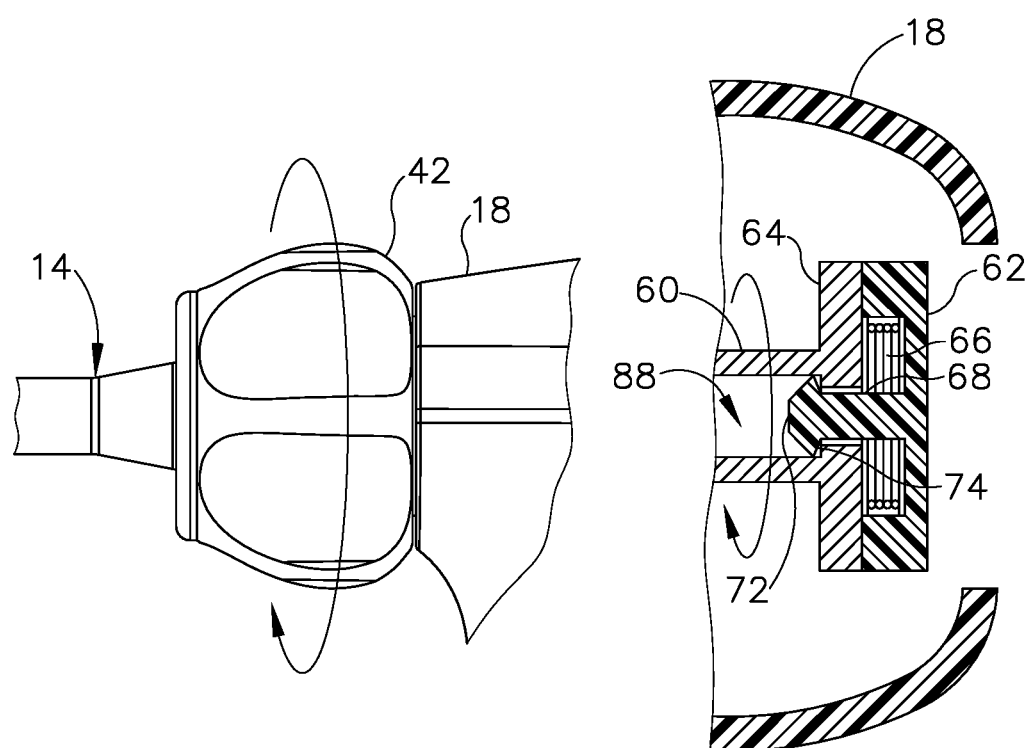
FIG. 7C depicts a side elevational view of a distal portion of the handle assembly of FIG. 7B and a schematic side sectional view of a proximal portion of the handle assembly, showing rotation of a rotation knob to thereby threadedly couple the waveguide with the ultrasonic transducer, and resulting rotation of the second wrench member of the integrated torque wrench mechanism relative to the first wrench member.

As described above, proximal wrench member (62) is rotationally fixed relative to body (18) of handle assembly (12), while distal wrench member (64) is rotatable relative to body (18) with ultrasonic transducer (26). As shown in FIG. 7C, rotation knob (42) may be rotated in a first direction to thereby rotate waveguide (38) relative to body (18). The frictional engagement of each tab (76) of proximal wrench member (62) with a cam ramp (82) of distal wrench member (64) generates a corresponding normal force and a resulting friction force between tabs (76) and cam ramps (82). This friction force limits the ability of ultrasonic transducer (26) to rotate with waveguide (38), thereby allowing waveguide (38) to rotate relative to transducer (26) and enabling threaded tip (58) of waveguide (38) to be threaded into threaded bore (56) of transducer (26) (see FIGS. 3A and 3B).

To achieve a secure and proper threaded coupling between waveguide (38) and ultrasonic transducer (26), without over-tightening or under-tightening, it is desirable to apply a predetermined maximum torque to the threaded coupling. The features of proximal and distal wrench members (62, 64) enable this result to be achieved without use of an external, separately provided torque wrench tool that might otherwise be lost or damaged over the course of one or more uses. In particular, as a user continues to rotate waveguide (38) into a tightened state relative to ultrasonic transducer (26), the torque required to be applied to waveguide (38) naturally increases. Increased torque applied to waveguide (38) is communicated to ultrasonic transducer (26) and ultimately to distal wrench member (64). When the applied torque is sufficient to overcome the initial friction forces exerted between tabs (76) and cam ramp bases (84), distal wrench member (64) begins to rotate with ultrasonic transducer (26) and waveguide (38) relative to proximal wrench member (62). As this occurs, tabs (76) ride along cam ramps (82) toward respective cam ramp peaks (86), thereby increasing the normal forces and resulting friction forces exerted between tabs (76) and cam ramps (82). The increased friction forces are overcome only by applying additional torque to waveguide (38), via rotation knob (42), which results in further tightening of waveguide (38) relative to ultrasonic transducer (26).

Tabs (76) and cam ramps (82) of torque wrench members (62, 64) exert a maximum normal force against one another, thereby generating a maximum friction force, when tabs (76) reach cam ramp peaks (86). The maximum friction force operates to limit rotation of ultrasonic transducer (26) relative to waveguide (38) and thereby enable further tightening of waveguide (38), as described above. Tabs (76) and cam ramps (82) are shaped such that the maximum friction force is overcome by applying a predetermined maximum torque to waveguide (38), and thus to the threaded coupling between waveguide (38) and ultrasonic transducer (26). The predetermined maximum torque is selected such that the threaded coupling is tightened to a degree sufficient to prevent unintended rotational loosening of waveguide (38) relative to ultrasonic transducer (26) during use, caused by under-tightening, and also to prevent failure of the threaded coupling during use, caused by over-tightening.

Figure 7D:
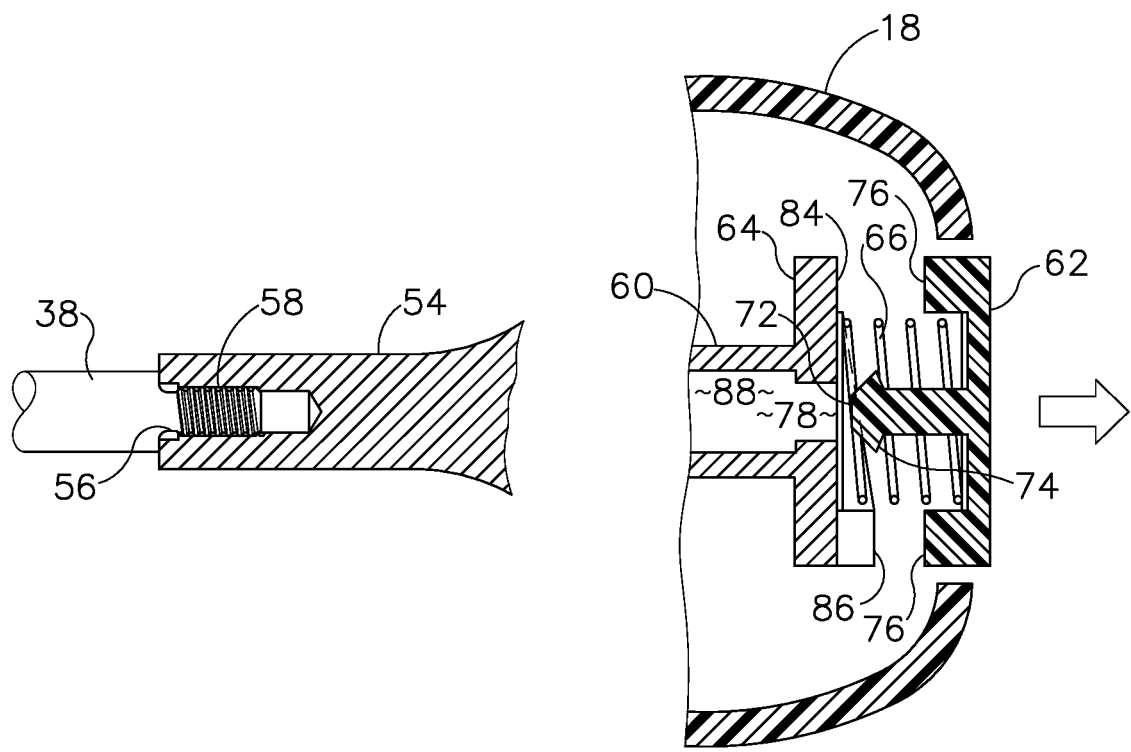
FIG. 7D depicts schematic side sectional views of proximal and distal portions of the ultrasonic surgical instrument of FIG. 7C, showing the waveguide fully threadedly coupled with the ultrasonic transducer via application of a predetermined maximum torque, and resulting decoupling of the first and second wrench members of the integrated torque wrench mechanism.

Upon application of the predetermined maximum torque to waveguide (38) and its threaded coupling with ultrasonic transducer (26), the maximum friction force is overcome and tabs (76) pass over cam ramp peaks (86) and snap against the adjacent cam ramp bases (84). As shown in FIG. 7D, tapered shoulder surface (74) of post (68) is suitably angled such that post (68) automatically releases proximally from opening (78) as a result of the maximum normal force, which acts as an axial separation force, exerted between tabs (76) and cam ramps (82), thereby decoupling wrench members (62, 64)

from one another. Upon this decoupling, compression spring (66) is able to expand and return proximal wrench member (62) to its proximal position.

The passing of tabs (76) over cam ramp peaks (86) and the decoupling of post (68) from opening (78) may generate an audible "clicking" or "snapping" sound and a corresponding tactile effect. This sound and tactile effect, in combination with the visual of proximal wrench member (62) returning to its proximal position, informs the user that the waveguide (38) and ultrasonic transducer (26) have been fully tightened together with the predetermined maximum torque. In this fully tightened state, wrench members (62, 64) remain engageable with one another in the same manner as described above. However, distal wrench member (64) will rotate freely relative to proximal wrench member (62) upon application of any torque greater than the maximum predetermined torque described above. In this manner, wrench members (62, 64) protect against overtightening of the threaded coupling between waveguide (38) and ultrasonic transducer (26).

II. EXEMPLARY ULTRASONIC SURGICAL INSTRUMENT HAVING INTEGRATED TORQUE WRENCH MECHANISM USABLE WITH EXTERNAL TOOL

Figure 8:
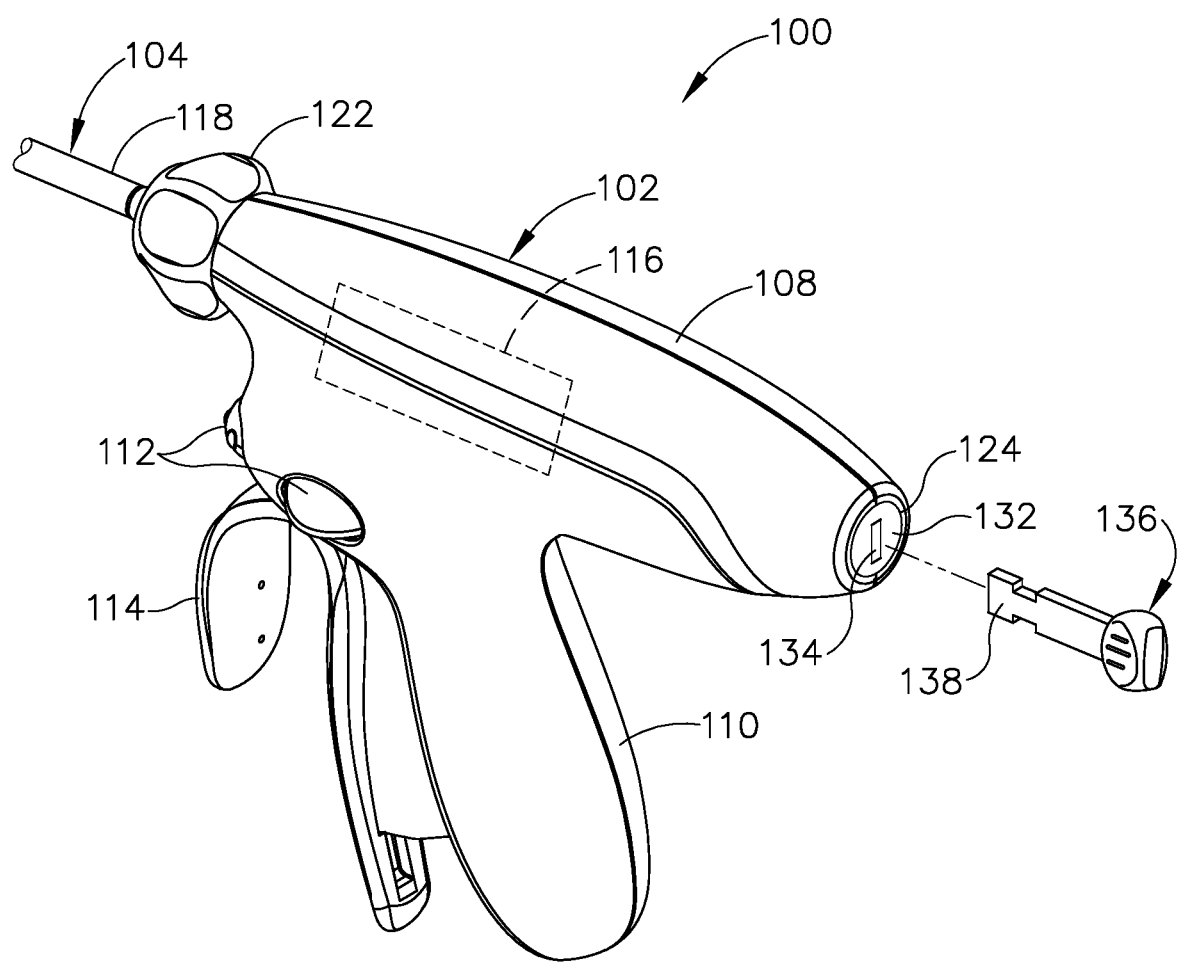
FIG. 8 depicts a rear perspective view of another exemplary ultrasonic surgical instrument having an integrated torque wrench mechanism operable in connection with an external tool.
Figure 9:
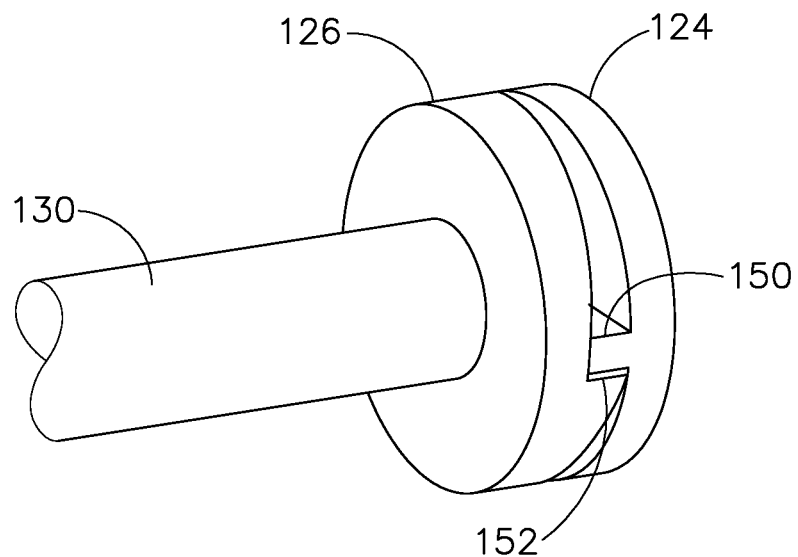
FIG. 9 depicts a perspective view of the integrated torque wrench mechanism of the ultrasonic surgical instrument of FIG. 8.
Figure 10:
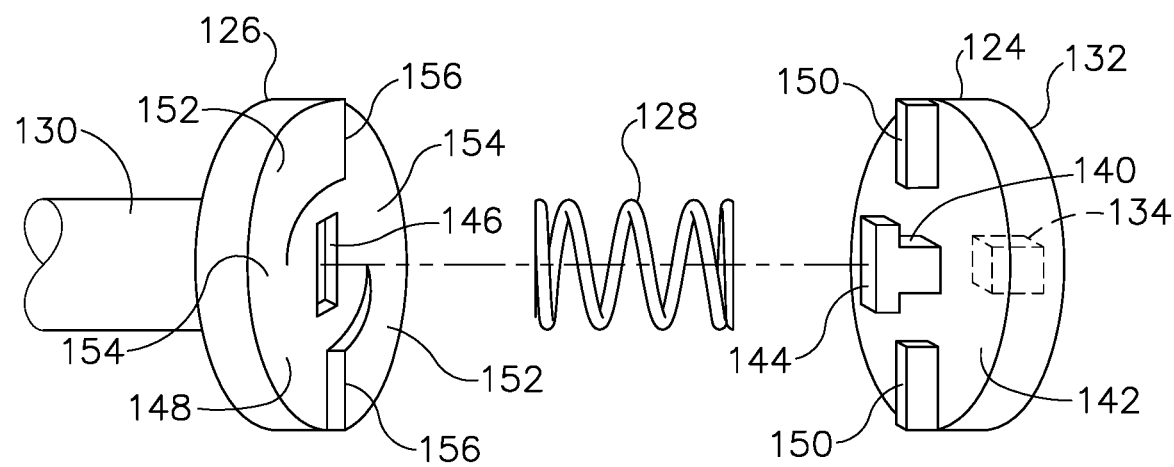
FIG. 10 depicts a disassembled perspective view of the integrated torque wrench mechanism of FIG. 9, showing first and second wrench members thereof and omitting a resilient member.

A. Exemplary Ultrasonic Surgical Instrument Having Integrated Torque Wrench Mechanism with Internal Keying Assembly FIGS. 8-10 show another exemplary ultrasonic surgical instrument (100) having an integrated torque wrench mechanism configured to facilitate threaded attachment of an ultrasonic waveguide to an ultrasonic transducer with a predetermined maximum torque. As described below, the integrated torque wrench mechanism is operable in combination with a separately provided key tool (136). Ultrasonic surgical instrument (100) and its integrated torque wrench mechanism are generally similar to surgical instrument (10) and its integrated torque wrench mechanism described above, except as otherwise described below.

Ultrasonic surgical instrument (100) is similar to surgical instrument (10) in that surgical instrument (100) includes a handle assembly (102), a shaft assembly (104) extending distally from handle assembly (102), and an end effector (not shown) arranged at a distal end of shaft assembly (104). Handle assembly (102) comprises a body (108) including a pistol grip (110) and energy control buttons (112) configured to be manipulated by a surgeon to control various aspects of tissue treatment energy delivered by surgical instrument (100). A trigger (114) is coupled to a lower portion of body (108) and is pivotable toward and away from pistol grip (110) to selectively actuate the end effector, which may be similar to end effector (16) described above. Body (108) houses an ultrasonic transducer (116), shown schematically in FIG. 8, configured to deliver ultrasonic energy to the end effector. Ultrasonic transducer (116) is rotatably mounted within body (108), and is generally similar in structure and function to ultrasonic transducer (26) described above.

Figure 11A:
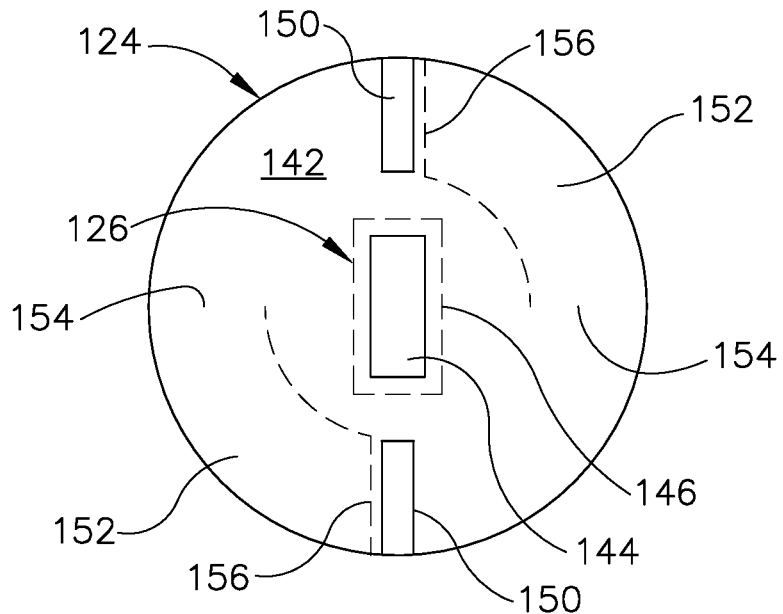
FIG. 11A depicts a schematic distal end view of the first and second wrench members of the integrated torque wrench mechanism of FIG. 10, showing the first and second wrench members in respective first rotational positions relative to a body of the ultrasonic surgical instrument, such that a projection of the first wrench member aligns with a recess of the second wrench member.
Figure 11B:
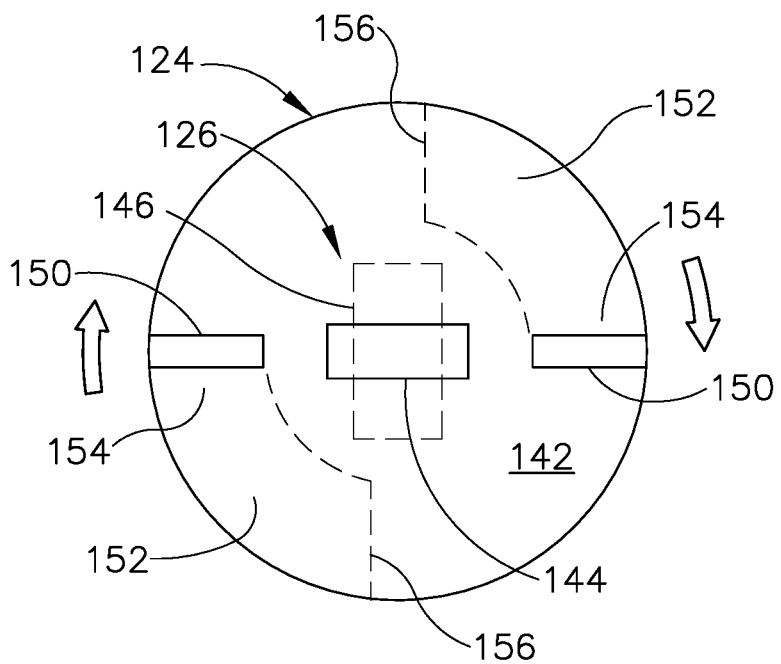
FIG. 11B depicts a schematic distal end view of the first and second wrench members of the integrated torque wrench mechanism of FIG. 11A, showing the first wrench member in a second rotational position in which the projection thereof lockingly engages the opening of the second wrench member.
Figure 11C:
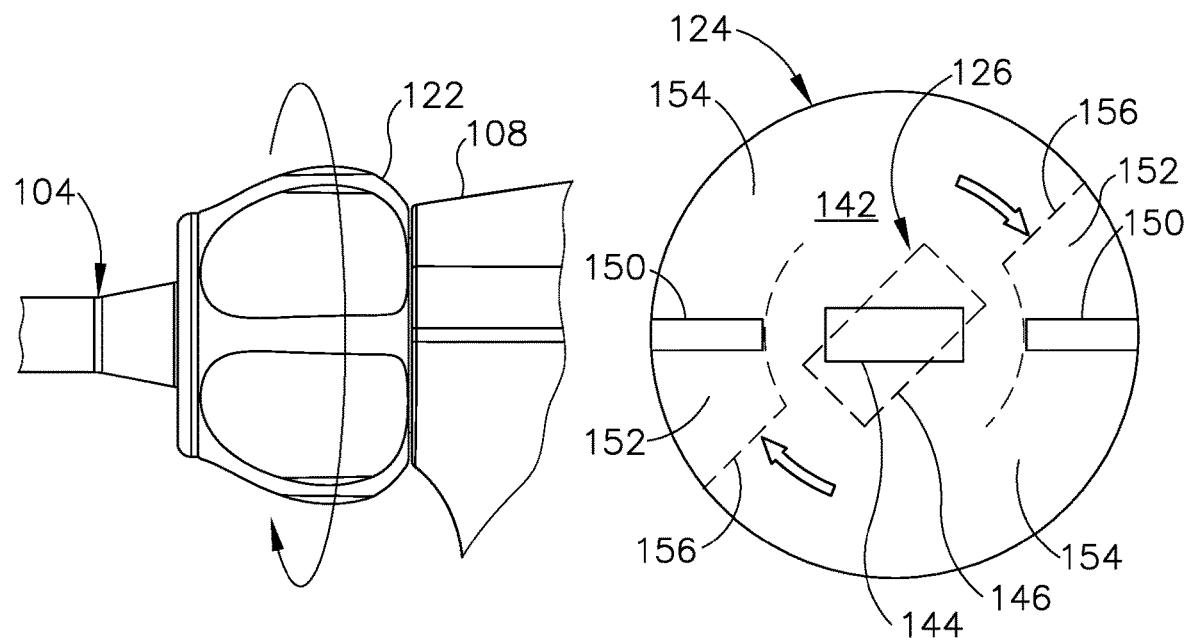
FIG. 11C depicts a side elevational view of a distal portion of a handle assembly of the ultrasonic surgical instrument of FIG. 11B and a schematic distal end view of the first and second wrench members of the integrated torque wrench mechanism, showing rotation of a rotation knob of the ultrasonic surgical instrument to thereby threadedly couple a waveguide thereof with an ultrasonic transducer thereof, and resulting rotation of the second wrench member of the integrated torque wrench mechanism relative to the first wrench member.
Figure 11D:
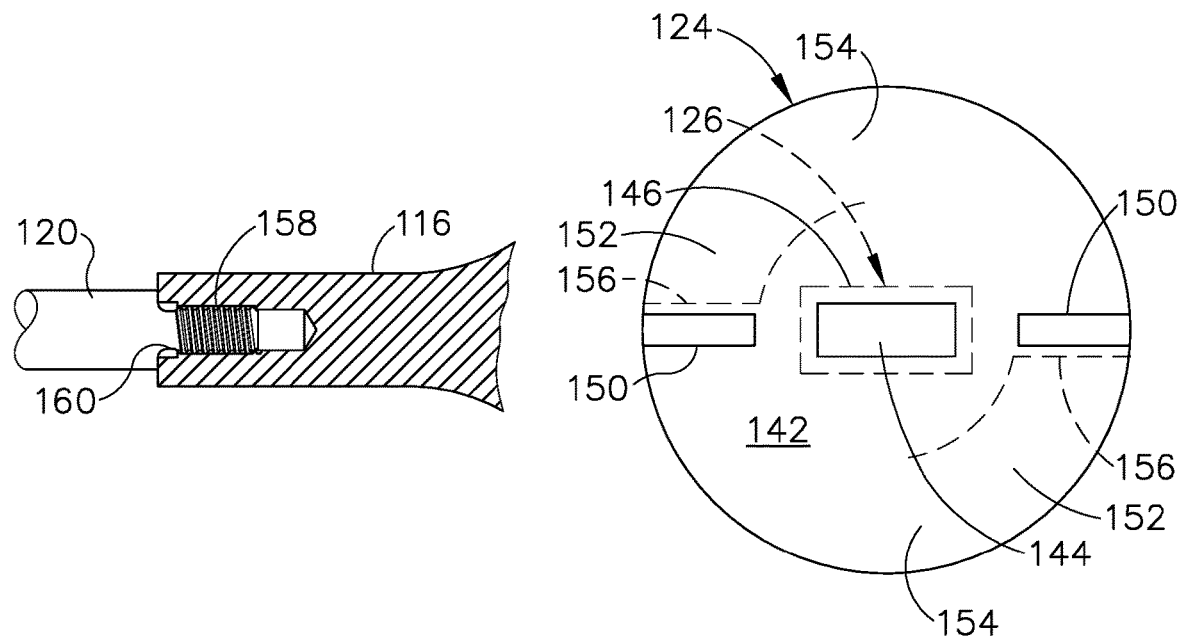
FIG. 11D depicts side sectional views of proximal and distal portions of the ultrasonic surgical instrument of FIG. 11C, showing the waveguide fully threadedly coupled with the ultrasonic transducer via application of a predetermined maximum torque, and resulting alignment of the projection of the first wrench member of the integrated torque wrench mechanism with the opening of the second wrench member to enable decoupling of the first and second wrench members.

Shaft assembly (104) is similar to shaft assembly (14) in that shaft assembly (104) includes an outer tube (118), an inner tube (not shown), and an ultrasonic waveguide (120) (see FIG. 11D). Waveguide (120) is similar in construction and function to waveguide (38) described above. In particular, waveguide (120) is configured to threadedly couple at its proximal end with a distal end of ultrasonic transducer (116), and is formed integrally at its distal end with an ultrasonic blade (not shown) similar to ultrasonic blade (28). Shaft assembly (104), including waveguide (120), is selectively rotatable about a longitudinal axis thereof by a rotation knob (122) that is similar to rotation knob (42) described above.

FIGS. 9 and 10 show details of an exemplary torque wrench mechanism integrated within a proximal end portion of ultrasonic surgical instrument (100). The torque wrench mechanism includes a proximal wrench member (124), a distal wrench member (126), and a compression spring (128) arranged therebetween. Wrench members (124, 126) are similar to wrench members (62, 64) described above in that wrench members (124, 126) are configured to frictionally engage one another to facilitate application of a predetermined maximum torque to the threaded coupling between ultrasonic transducer (116) and waveguide (120). Unique features and functionality of wrench members (124, 126) are described in greater detail below.

Proximal wrench member (124) is in the form of a disk-like structure coupled to a proximal end of body (108) of handle assembly (102), and distal wrench member (126) is in the form of a disk-like structure that defines, or is otherwise affixed to, a proximal end of a transducer coupling member (130) extending proximally from ultrasonic transducer (116). In the present example, proximal wrench member (124) is configured to translate proximally and distally, as well as rotate, relative to body (108) and distal wrench member (126). Distal wrench member (126) is configured to rotate relative to body (108) with ultrasonic transducer (116), and is generally fixed longitudinally. Compression spring (128) is configured to resiliently bias proximal wrench member (124) proximally, away from distal wrench member (126).

As shown in FIG. 8, a proximal face (132) of proximal wrench member (124) is exposed through an opening formed in a proximal end of body (108) of handle assembly (102). Proximal face (132) includes a keyway (134) configured to receive a key element (138) formed on a key tool (136) provided separately from ultrasonic surgical instrument (100). As such, keyway (134) and key element (138) cooperate to define an external keying assembly of surgical instrument (100). Key element (138) is insertable into external keyway (134) to rotate proximal wrench member (124) relative to distal wrench member (126) and thereby releasably couple wrench members (124, 126) together. Surgical instrument (100) may include a detent mechanism (not shown) or a similar locking structure configured to retain proximal wrench member (124) in a selected rotational orientation relative to distal wrench member (126).

As shown best in FIG. 10, proximal wrench member (124) includes a centrally arranged post (140) projecting distally from a distal face (142) of proximal wrench member (124). Post (140) includes a head (144) configured to be received within a centrally arranged opening (146) formed in a proximal face (148) of distal wrench member (126). Post head (144) and opening (146) are each formed with similar, or at least partially complementary shapes such that head (144) is passable through opening (146) only when head (144) and opening (146) are rotationally aligned with one another. In the present example, head (144) and opening (146) are each rectangular in shape, though it will be understood that various other shapes may be used. Head (144) and opening (146) cooperate to define an internal keying assembly of surgical instrument (100) in which head (144) functions as a key element and opening (146) functions as a keyway. As described in greater detail below with reference to FIGS. 11A-11D, once inserted distally through opening (146) and into an internal bore (not shown) of transducer coupling member (130), post head (144) is rotatable relative to distal wrench member (126) to releasably couple wrench members (124, 126) together. Compression spring (128) is arranged coaxially with post (140) and opening (146) such that a proximal spring end confronts distal face (142) of proximal wrench member (124), a distal spring end confronts proximal face (148) of distal wrench member (126), and post (140) extends distally through spring (128) in manner similar to that shown in FIGS. 7A and 7B.

Proximal wrench member (124) further includes a pair of tabs (150) similar in structure and function to tabs (76) described above. Tabs (150) project distally from distal face (142) at diametrically opposed locations, and are configured to function as cam follower elements, as described below. Distal wrench member (126) includes a pair of cam ramps (152) configured to frictionally engage tabs (150) in a manner similar to cam ramps (82) described above. Cam ramps (152) extend circumferentially about proximal face (148), and each cam ramp (152) includes a ramp base (154) and a ramp peak (156) that is elevated proximally beyond the respective ramp base (154). Each ramp base (154) may lie substantially flush with proximal face (148). In the present example, each cam ramp (152) extends from its ramp base (154) to its ramp peak (156) along a circumferential path passing through a 90-degree quadrant of proximal face (148). Consequently, as shown in FIG. 10, ramp peaks (156) are diametrically opposed from one another along a first plane, and ramp bases (154) are diametrically from one another along a second plane extending perpendicularly to the first plane. Other versions of ultrasonic surgical instrument (100) may include various other suitable arrangements and/or quantities of post (140), opening (146), tabs (150), and cam ramps (152). For example, post (140) and tabs (150) may be arranged on distal wrench member (126), and cam ramps (152) and opening (146) may arranged on proximal wrench member (124).

B. Exemplary Method for Threadedly Coupling Waveguide with Ultrasonic Transducer Using Integrated Torque Wrench Mechanism and External Tool FIGS. 11A-11D show an exemplary method of threadedly coupling waveguide (120) with ultrasonic transducer (116) using integrated torque wrench members (124, 126) described above to facilitate application of a predetermined maximum torque to the threaded coupling. FIG. 11A shows proximal wrench member (124) arranged in a first rotational orientation relative to distal wrench member (126), in which post head (144) of proximal wrench member (124) is rotationally aligned with and is insertable through opening (146) of distal wrench member (126). Post head (144) is directed distally through opening (146) by depressing proximal wrench member (124) distally relative to body (108) of handle assembly (102) using external key tool (136) inserted into external keyway (134) (see FIG. 8). This step includes compressing compression spring (128) between proximal and distal wrench members (124, 126). As shown in FIG. 11B, proximal wrench member (124) is then rotated 90 degrees, by external key tool (136), relative to distal wrench member (126) to thereby lock post head (144) within opening (146) and to align tabs (150) with cam ramp bases (154). Key tool (136) may then be removed from external keyway (134). Proximal wrench member (124) may be maintained in its rotational orientation by an internal detent mechanism (not shown) or a functionally similar locking mechanism, as described above.

As shown in FIG. 11C, while proximal wrench member (124) remains rotationally fixed, rotation knob (122) is rotated (e.g., clockwise) to rotate waveguide (120) relative to handle assembly (102). Tabs (150) of proximal wrench member (124) frictionally engage cam ramp bases (154) of distal wrench member (126) to exert an initial normal force and generate a corresponding initial friction force that limits the ability of ultrasonic transducer (116) to rotate with waveguide (120). As a result, waveguide (120) is permitted to rotate relative to transducer (116), thereby threading proximal threaded tip (158) of waveguide (120) into distal threaded bore (160) of transducer (116). As the user continues to increase the input torque applied to waveguide (120) to thereby further tighten the threaded coupling between waveguide (120) and transducer (116), the friction forces exerted between tabs (150) and cam ramps (152) are progressively overcome. This allows distal wrench member (126) to rotate with transducer (116) and waveguide (120) relative to proximal wrench member (124). This rotation causes tabs (150) to travel circumferentially along cam ramps (152) closer toward cam ramp peaks (156), while allowing opening (146) to rotate closer into rotational alignment with post head (144).

As tabs (150) travel along cam ramps (152) toward cam ramp peaks (156), the normal force and resulting friction force exerted between tabs (150) and cam ramps (152) progressively increase. To overcome the progressively increasing friction force, progressively greater torque must be applied to waveguide (120) via rotation knob (122), thereby further threadedly tightening waveguide (120) relative to ultrasonic transducer (116). As tabs (150) reach cam ramp peaks (156), tabs (150) and cam ramps (152) generate a maximum friction force that is overcome by applying a predetermined maximum torque to waveguide (120) via rotation knob (122). Upon application of this predetermined maximum torque, waveguide (120) becomes fully threadedly tightened relative to ultrasonic transducer (116), tabs (150) pass over cam ramp peaks (156), and opening (146) rotates into alignment with post head (144), as shown in FIG. 11D. In this rotational position of distal wrench member (126), post head (144) is releasable proximally from opening (146) and compression spring (128) expands to automatically return proximal wrench member (124) to its proximal position and thereby decouple proximal wrench member (124) from distal wrench member (126).

The passing of tabs (150) over cam ramp peaks (156), as well as the disengagement and proximal return of proximal wrench member (124) may create an audible "clicking" or "snapping" sound and a corresponding tactile effect. This sound and tactile effect, in combination with the visual of proximal wrench member (124) returning proximally, informs the user that the waveguide (120) and ultrasonic transducer (116) have been fully tightened to the predetermined maximum torque and that surgical instrument (100) is ready for use. As described above in connection with surgical instrument (10), the predetermined maximum torque permitted by torque wrench members (124, 126) of surgical instrument (100) is selected such that the threaded coupling between waveguide (120) and transducer (116) is tightened to a degree sufficient to prevent rotational loosening of waveguide (120) relative to transducer (116) during use, and also to prevent failure of the threaded coupling during use. In the fully tightened state, wrench members (124, 126) remain engageable with one another in the same manner as described above. However, distal wrench member (126) will rotate freely relative to proximal wrench member (124) upon application of any torque greater than the maximum predetermined torque. In this manner, wrench members (124, 126) protect against overtightening of the threaded coupling between waveguide (120) and ultrasonic transducer (116).

Figure 12:
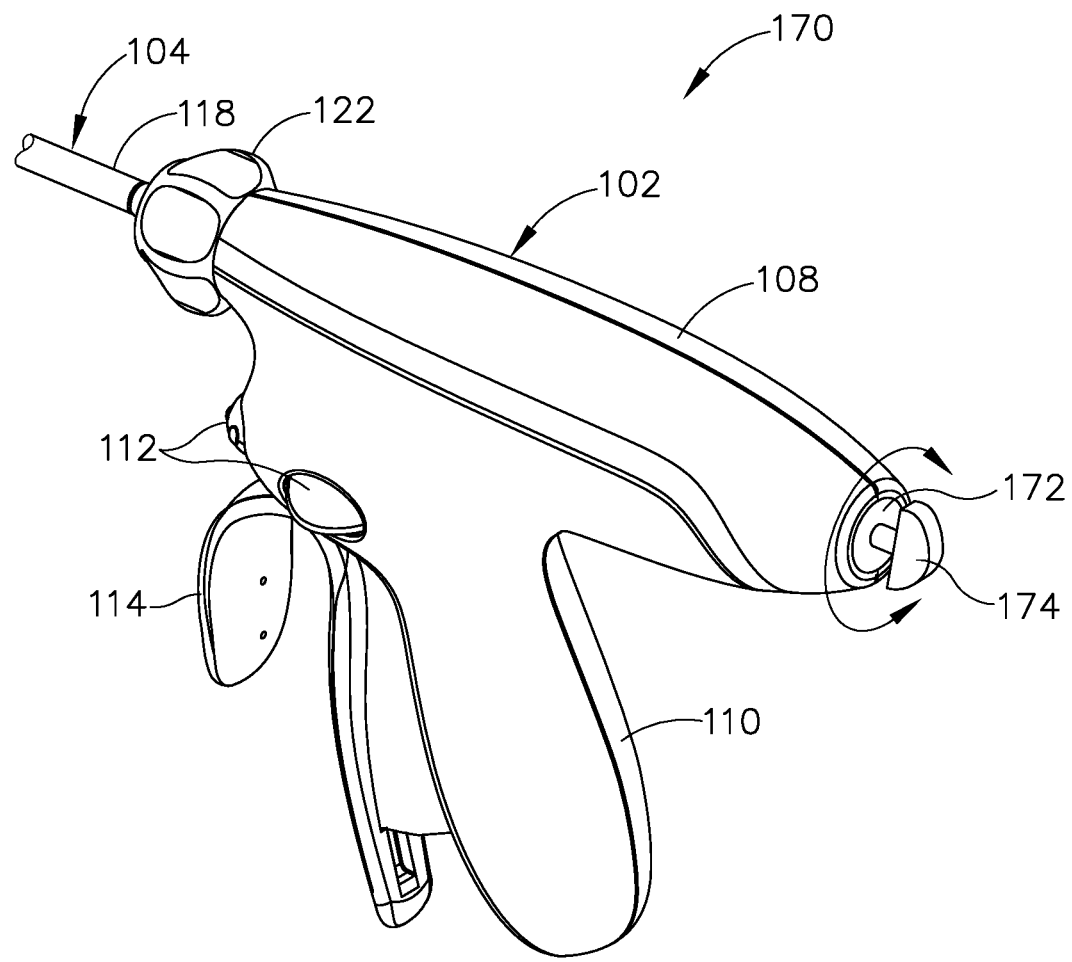
FIG. 12 depicts a rear perspective view of another exemplary ultrasonic surgical instrument having an integrated torque wrench mechanism with a user engageable knob.

C. Ultrasonic Surgical Instrument Having Exemplary Alternative Integrated Torque Wrench Mechanism FIG. 12 shows another exemplary ultrasonic surgical instrument (170) having an integrated torque wrench mechanism. As indicated by use of like reference numerals, surgical instrument (170) is similar to surgical instrument (100) in all aspects except that surgical instrument (170) includes a proximal wrench member (172) that omits external keyway (134) and instead includes a user engageable wrench knob (174) that is formed integrally with and projects proximally from proximal wrench member (172). Wrench knob is configured to be gripped by a user and rotated to thereby rotate proximal wrench member (172) relative to distal wrench member (126) to thereby couple wrench members (126, 172) together in a manner similar to that described above in connection with FIG. 11B. While wrench knob (174) of the present example is shown in the form of a generally t-shaped structure, it will be appreciated that wrench knob (174) may take on various other shapes suitable to be gripped by a user. For example, in some versions knob (174) may be similar in shape to rotation knob (122).

III. EXEMPLARY ULTRASONIC SURGICAL INSTRUMENT HAVING ATTACHABLE PROXIMAL DRIVE ASSEMBLY WITH INTEGRATED TORQUE WRENCH MECHANISM

Figure 13:
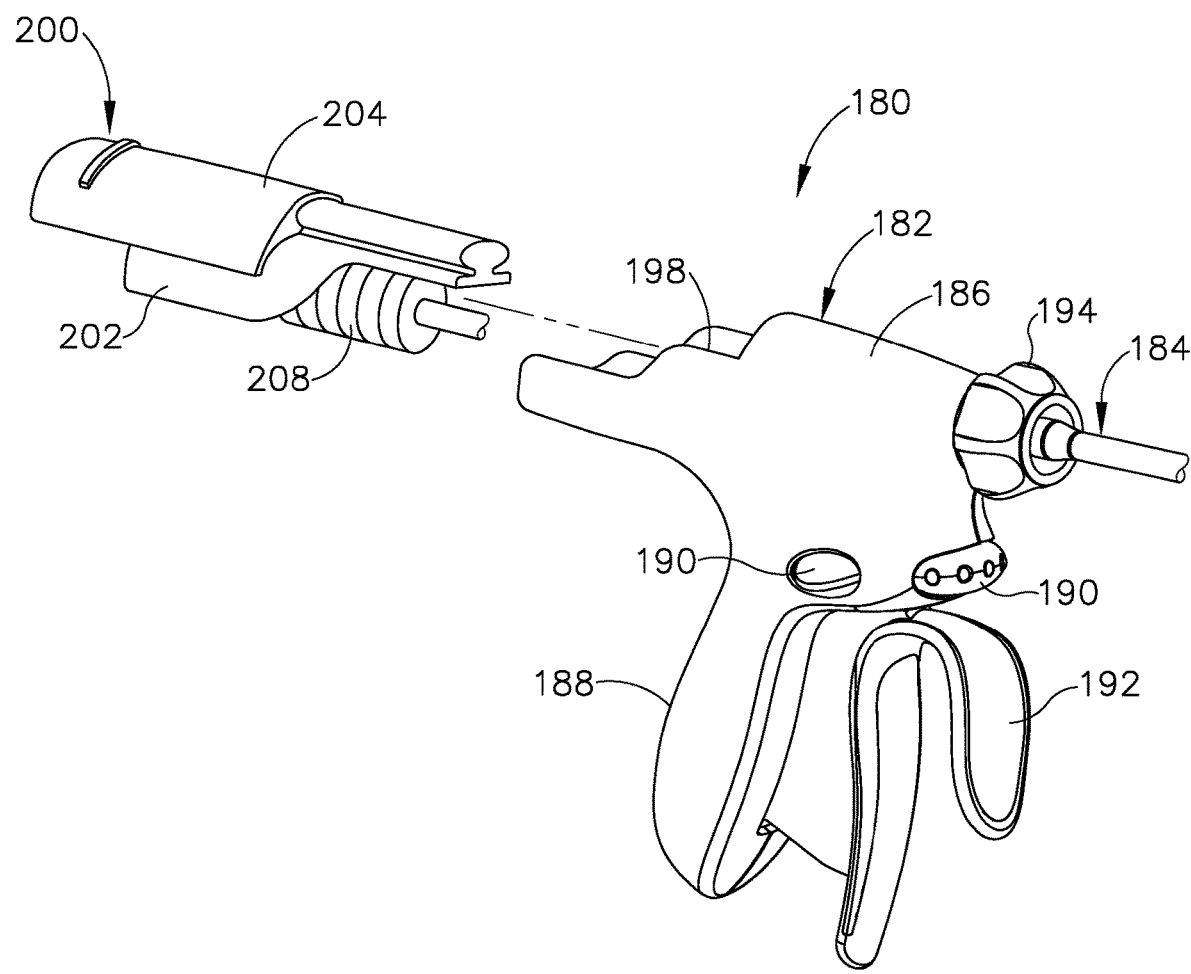
FIG. 13 depicts a partially disassembled perspective view of another exemplary ultrasonic surgical instrument including a proximal drive assembly having an integrated torque wrench mechanism.
Figure 14:
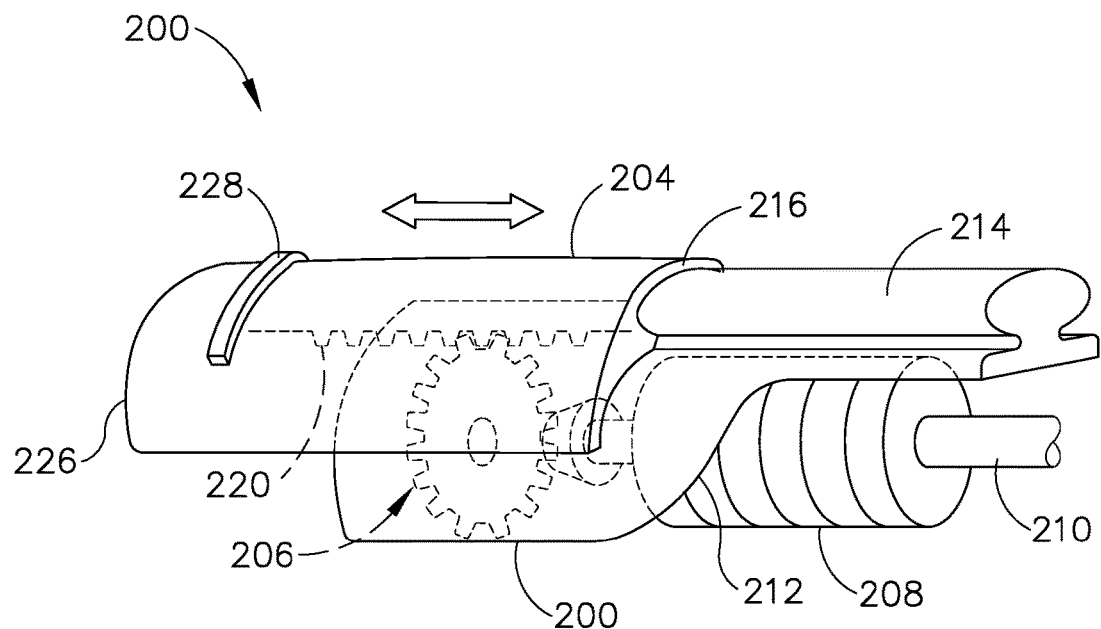
FIG. 14 depicts a perspective view of the proximal drive assembly of FIG. 13, showing details of a translatable push arm, an ultrasonic transducer, and rack and gear components of the proximal drive assembly.
Figure 15:
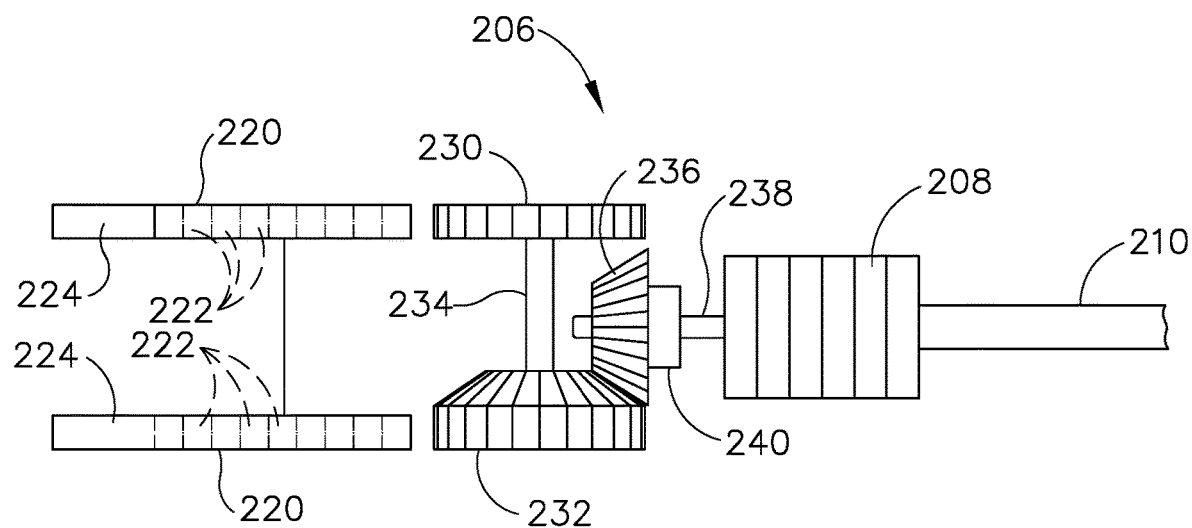
FIG. 15 depicts a top elevational view of the proximal drive assembly of FIG. 14, with the translatable push arm being omitted in part.

A. Exemplary Ultrasonic Surgical Instrument and Integrated Torque Wrench Mechanism FIGS. 13-15 show another exemplary ultrasonic surgical instrument (180) having an integrated torque wrench mechanism configured to facilitate threaded attachment of an ultrasonic waveguide to an ultrasonic transducer with a predetermined maximum torque. Ultrasonic surgical instrument (180) is similar to surgical instruments (10, 100) described above in that surgical instrument (180) includes a handle assembly (182), a shaft assembly (184) extending distally from handle assembly (182), and an end effector (not shown) arranged at a distal end of shaft assembly (184). Handle assembly (182) comprises a body (186) including a pistol grip (188) and energy control buttons (190) configured to be manipulated by a surgeon to control various aspects of tissue treatment energy delivered by surgical instrument (180). A trigger (192) is coupled to a lower portion of body (186) and is pivotable toward and away from pistol grip (188) to selectively actuate the end effector, which may be similar to end effector (16) described above. A rotation knob (194) is rotatably coupled to a distal end of body (186) and is rotatable with shaft assembly (184), including a waveguide (196) thereof (see FIG. 16B), relative to body (186) about a longitudinal axis defined by shaft assembly (184). A proximal end of body (186) includes an opening (198) configured to receive a proximal drive assembly (200). As described in greater detail below, features of proximal drive assembly (200) define an integrated torque wrench mechanism.

FIGS. 14 and 15 show additional details of proximal drive assembly (200), which includes a frame (202), a push arm (204) slidably coupled to an upper end of frame (202), and a gear assembly (206) and ultrasonic transducer (208) supported within an interior of frame (202). As described in greater detail below, push arm (204) and gear assembly (206) cooperate to define a torque wrench mechanism integrated within surgical instrument (180). Ultrasonic transducer (208) may be generally similar in structure and function to ultrasonic transducer (26) described above, including having an internally threaded distal end (210), and is rotatably supported by frame (202). As shown in FIG. 14, frame (202) includes a contoured distal edge (212) configured to confront corresponding features of handle assembly body (186). An upper end of frame (202) includes a linear track (214) along which an upper carriage portion (216) of push arm (204) is configured to translate between proximal and distal positions. As described in greater detail below, translation of push arm (204) relative to frame (202) operates to rotate ultrasonic transducer (208) into or out of threaded engagement with a threaded proximal end (218) of waveguide (196) (see FIG. 16B). Linear track (214) and upper carriage portion (216) are formed with complementary cross-sectional shapes, which enables push arm (204) and frame (202) to remain engaged with one another throughout a full stroke of push arm (204).

Figure 16A:
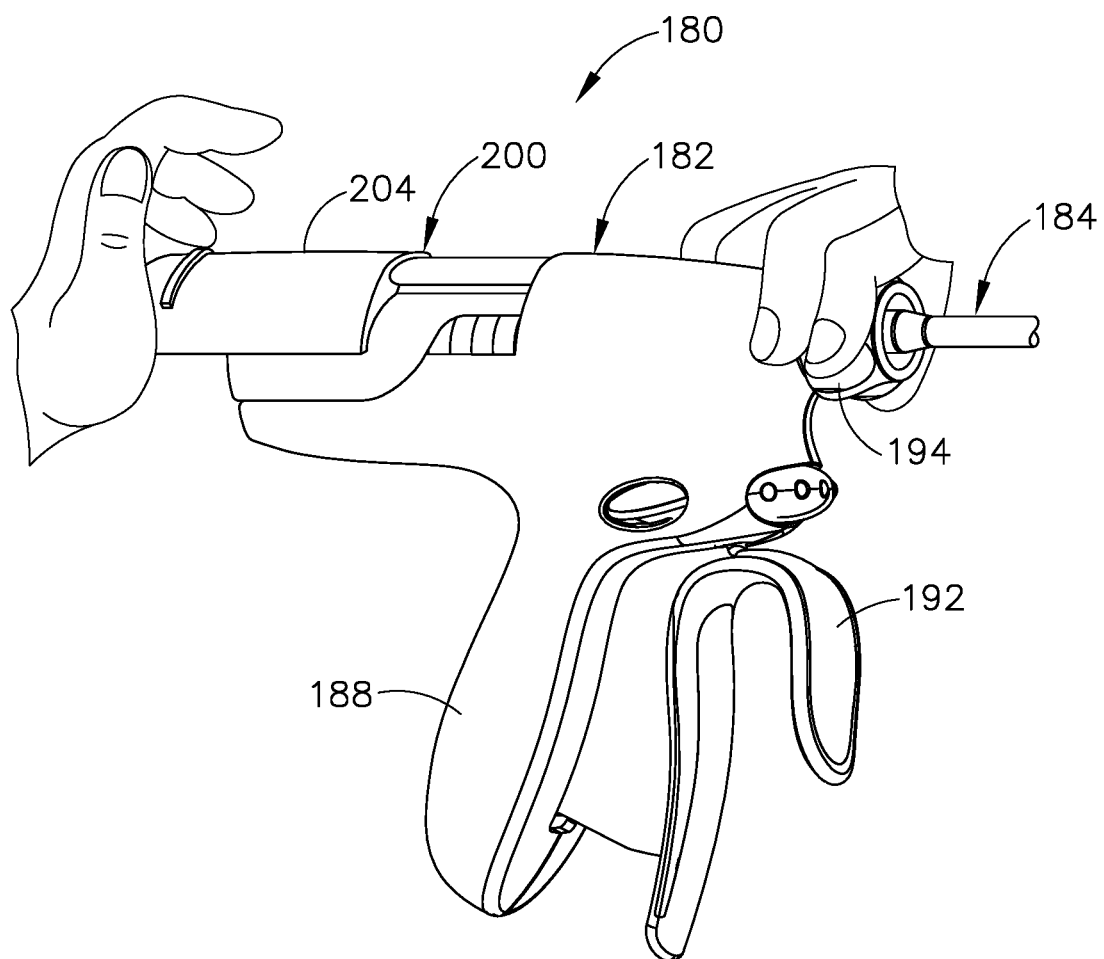
FIG. 16A depicts a schematic perspective view showing the proximal drive assembly of FIG. 14 being assembled with a handle assembly of the ultrasonic surgical instrument of FIG. 13, and the push arm being translated distally.

Push arm (204) further includes a pair of downwardly facing linear racks (220) extending longitudinally along an underside of upper carriage portion (216) within an interior of push arm (204). Each rack (220) has a plurality of teeth (222) configured to engage upper portions of gear assembly (206). Optionally, each rack (220) may include a proximal toothless portion (224) that decouples rack (220) from gear assembly (206) when push arm (204) is in its distal position, as described below in connection with FIG. 17C. Push arm (204) further includes a closed distal end (226) that facilitates pushing of push arm (204) from its proximal position toward its distal position during attachment of proximal drive assembly (200), as shown in FIG. 16A described below. Additionally, push arm (204) includes a gripping element (228) arranged an upper surface thereof that facilitates pulling of push arm (204) from its distal position toward its proximal position during removal of proximal drive assembly (200), as shown in FIG. 18A described below.

As shown best in FIG. 15, gear assembly (206) includes a first gear (230) and a second gear (232) rotationally coupled with one another by a gear shaft (234) mounted to frame (202) and extending transversely to racks (220). Gear assembly (206) further includes a third gear (236) mounted to a proximal transducer shaft (238) coupled to ultrasonic transducer (208). Third gear (236) is positioned distally of and couples with second gear (232). In the present example, second and third gears (232, 236) are shown in the form of bevel gears, and are configured to rotate about respective axes extending perpendicularly to one another. As described in greater detail below, gears (230, 232, 236) cooperate with racks (220) to transform linear motion of push arm (204) into rotational motion of ultrasonic transducer (208), and thereby threadedly couple or decouple transducer (208) with waveguide (196).

As shown schematically in FIG. 15, third gear (236) incorporates a one-way slip ratchet mechanism (240) configured to rotationally decouple third gear (236) from proximal transducer shaft (238) and thereby allow third gear (236) to rotate freely relative to ultrasonic transducer (208) when a predetermined maximum torque is applied to third gear (236) via distal movement of push arm (204) and racks (220). In this manner, one-way slip ratchet mechanism (240) cooperates with the surrounding components of proximal drive assembly (200) to define an integrated torque wrench mechanism.

Figure 16B:
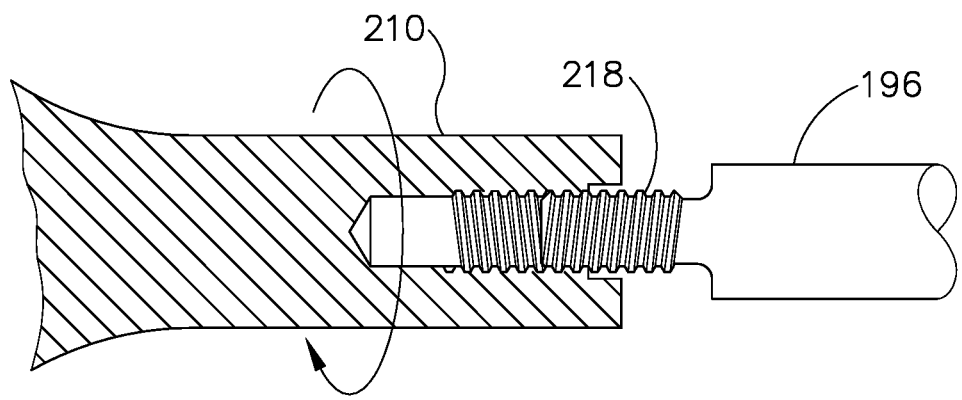
FIG. 16B depicts a side sectional view showing a distal end of an ultrasonic transducer of the ultrasonic surgical instrument of FIG. 16A being threadedly coupled with a waveguide thereof upon distal translation of the translatable push arm.

B. Exemplary Method for Threadedly Coupling Waveguide with Ultrasonic Transducer Using Features of Proximal Drive Assembly FIGS. 16A-17C show steps of an exemplary method for threadedly coupling together waveguide (196) and ultrasonic transducer (208) of ultrasonic surgical instrument (180) using the features of proximal drive assembly (200) described above. FIG. 16A shows proximal drive assembly (200) being mated with body (186) of handle assembly (182) such that ultrasonic transducer (208) and a corresponding distal portion of proximal drive assembly (200) is received at least partially within body (186) through proximal opening (198). Proximal drive assembly (200) and proximal opening (198) are constructed with complementary shapes such that mating of proximal drive assembly (200) with handle assembly (182) positions threaded distal end of ultrasonic transducer (208) in axial alignment with threaded proximal end (218) of waveguide (196). As shown in FIG. 16A, a user then holds waveguide (196) in a rotationally fixed position by gripping rotation knob (194). Simultaneously, the user drives push arm (204) distally to rotate ultrasonic transducer (208) in a first direction (e.g., clockwise) relative to the rotationally stationary waveguide (196), thereby rotating ultrasonic transducer (208) into threaded engagement with waveguide (196), as shown in FIG. 16B. Though not shown, proximal drive assembly (200) may include a locking mechanism that maintains push arm (204) in its proximal position until proximal drive assembly (200) is mated with handle assembly (182).

Figure 17A:
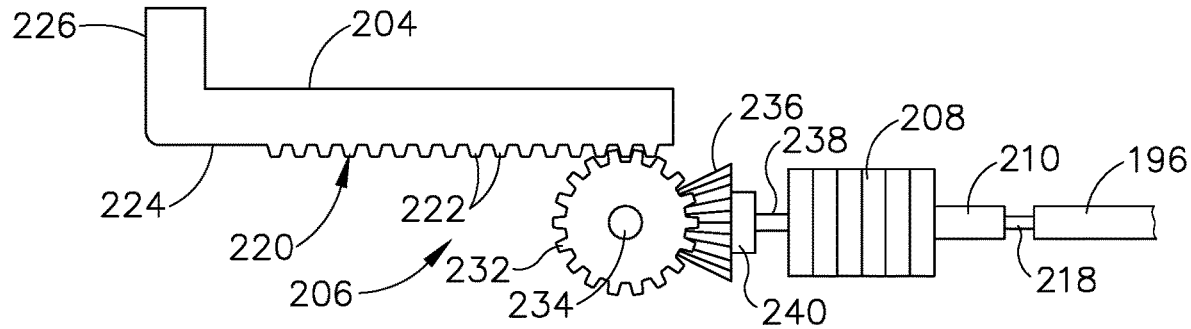
FIG. 17A depicts a schematic side view of the proximal drive assembly and a proximal end of the waveguide of the ultrasonic surgical instrument of FIG. 16A, showing the push arm in a proximal position in which the rack engages a first gear which in turn engages a second gear coupled to the ultrasonic transducer.
Figure 17B:
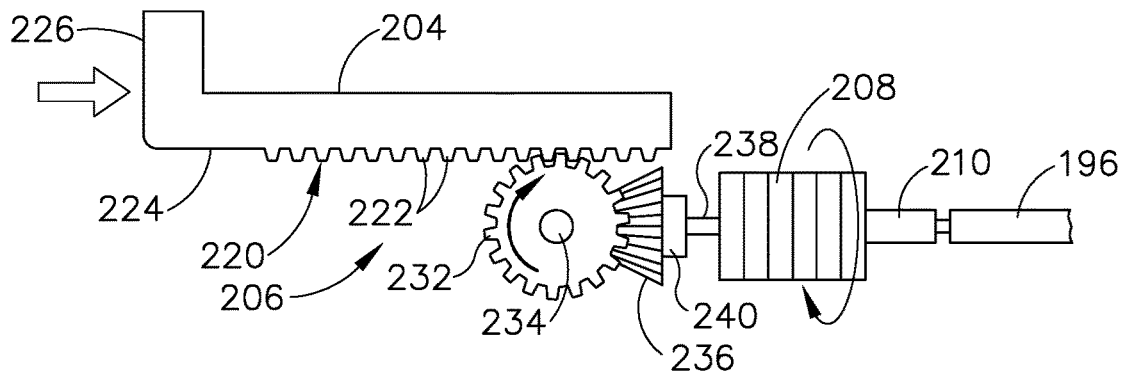
FIG. 17B depicts a schematic side view of the proximal drive assembly and the waveguide proximal end of FIG. 17A, showing the push arm being translated distally to thereby rotate the gears and the ultrasonic transducer relative to the waveguide to thereby threadedly couple the ultrasonic transducer with the waveguide.
Figure 17C:
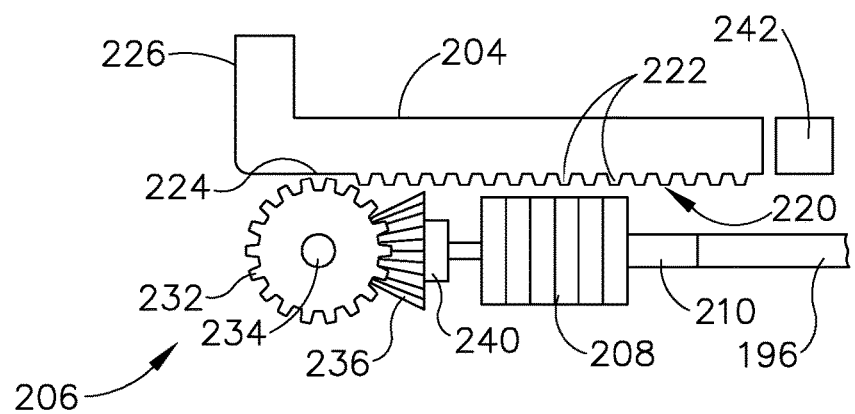
FIG. 17C depicts a schematic side view of the proximal drive assembly and the waveguide proximal end of FIG. 17B, showing the push arm in a distal position in which the rack disengages the gears and the ultrasonic transducer is fully threadedly coupled with the waveguide.
Figure 18A:
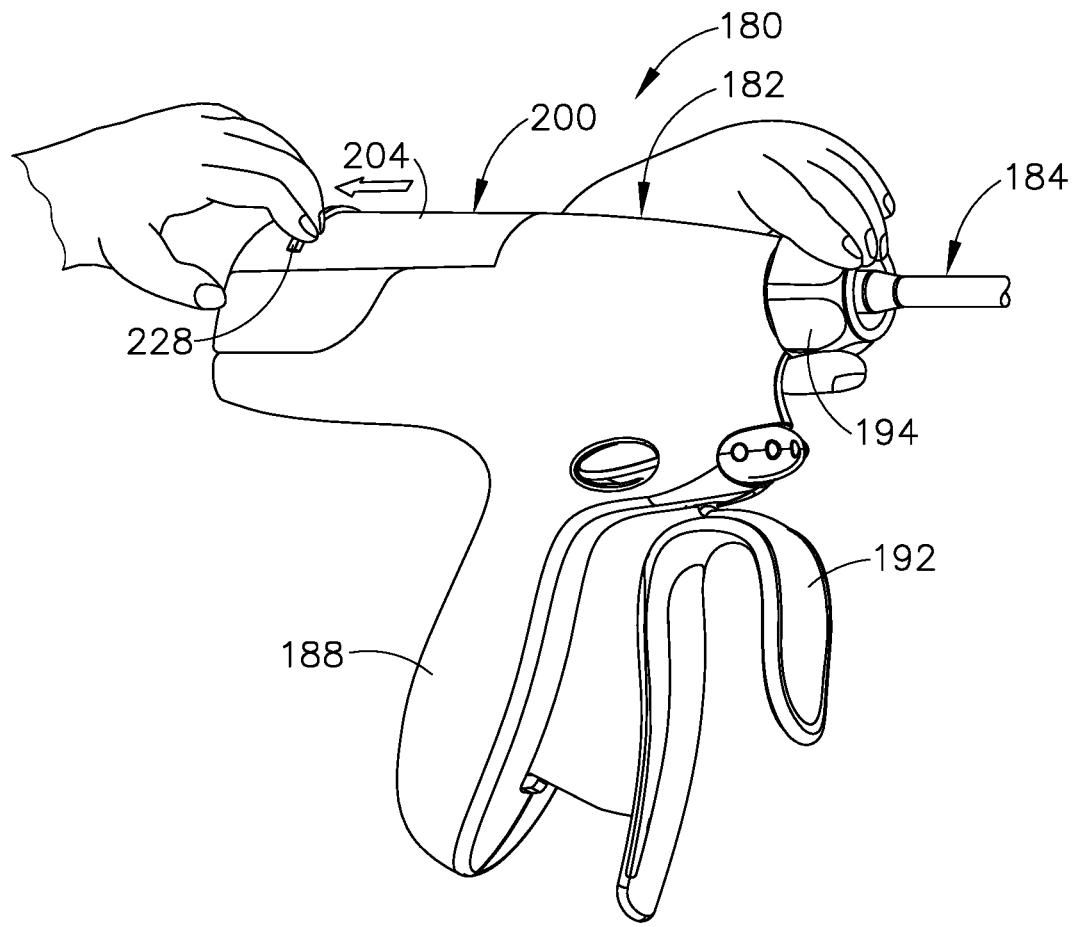
FIG. 18A depicts a schematic perspective view of the ultrasonic surgical instrument of FIG. 13, showing the push arm being translated proximally to decouple the ultrasonic transducer from the waveguide.

FIGS. 17A-17C show interaction of the components of proximal drive assembly (200) as push arm (204) is driven distally from its proximal position. FIG. 17A shows push arm (204) in a proximal position in which distal ends of racks (220) engage first and second gears (230, 232) of gear assembly (206), and in which ultrasonic transducer (208) is not yet threadedly coupled with waveguide (196). FIG. 17B shows push arm (204) being driven distally toward its distal position, thereby causing first and second racks (220) to exert a torque on and rotate first and second gears (230, 232) in a first direction (e.g., clockwise) about their shaft axis. Second gear (232) transfers this torque to third gear (236), thereby causing third gear (236) to rotate in the first direction about its shaft axis. Because third gear (236) is rotationally coupled with ultrasonic transducer (208) as described above, torque exerted on third gear (236) is transferred to transducer (208) via proximal transducer shaft (238), thereby causing transducer (208) to rotate in the first direction relative to waveguide (196). Meanwhile, waveguide (196) is being held rotationally stationary as described above. Accordingly, the relative rotation between transducer (208) and waveguide (196) causes threaded distal end of transducer (208) to threadedly couple with threaded proximal end (218) of waveguide (196). In this manner, the input torque exerted on first and second gears (230, 232), by translating push arm (204) and racks (220), is ultimately transferred to the threaded coupling between transducer (208) and waveguide (196).

Continued distal advancement of push arm (204) causes transducer (208) to thread into further, tighter engagement with waveguide (196). When the torque exerted on third gear (236), and thus on the threaded coupling between transducer (208) and waveguide (196), reaches a predetermined maximum, one-way slip ratchet mechanism (240) rotationally decouples third gear (236) from ultrasonic transducer (208). In this manner, input torque exceeding the predetermined maximum value is prevented from transferring to the threaded coupling between transducer (208) and waveguide (196), thereby protecting against overtightening of the threaded coupling.

FIG. 17C shows push arm (204) in its distal position in which proximal toothless portions (224) of racks (220) overlie first and second gears (230, 232) such that racks (220) are decoupled from gear assembly (206). This configuration prevents further rotation of gears (230, 232, 236) in the first direction and further tightening of transducer (208) relative to waveguide (196). In some versions of ultrasonic surgical instrument (180), one-way slip ratchet mechanism (240) may be omitted. In such versions, racks (220) and their proximal toothless portions (224) may be formed with suitable lengths such that a full distal stroke of push arm (204) from its proximal position to its distal position yields a quantity of rotations of ultrasonic transducer (208) relative to waveguide (196) that achieves application of a predetermined maximum torque to the threaded coupling between transducer (208) and waveguide (196). As shown schematically in FIG. 17C, surgical instrument (180) includes a push arm detent mechanism (242) configured to releasably retain push arm (204) in its distal position to prevent unintended proximal retraction of push arm (204), and corresponding decoupling of transducer (208) from waveguide (196) during use of surgical instrument (180).

Figure 18B:
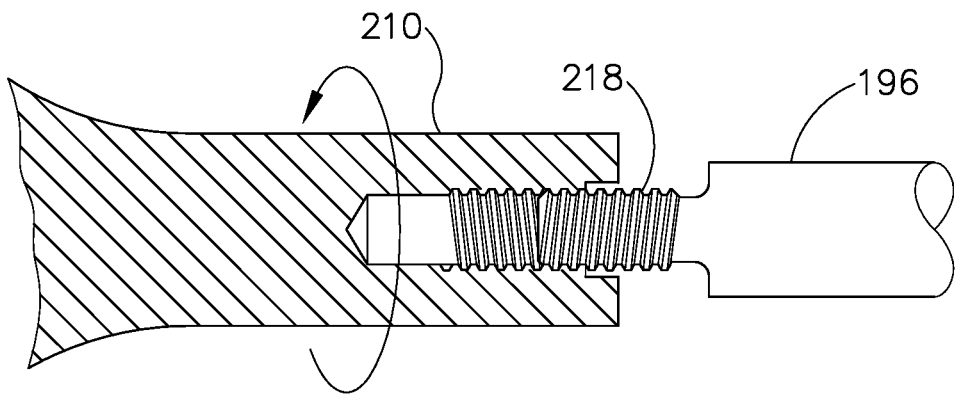
FIG. 18B depicts a side sectional view showing a distal end of the ultrasonic transducer of the ultrasonic surgical instrument of FIG. 18A being threadedly decoupled from the waveguide upon proximal translation of the push arm.

In various circumstances, it may be desirable to decouple ultrasonic transducer (208) from waveguide (196) and remove proximal drive assembly (200) from handle assembly (182), for example after completion of one or more surgical procedures using ultrasonic surgical instrument (180). An exemplary decoupling process is shown in FIGS. 18A and 18B. In particular, the user fixes waveguide (196) rotationally, for example by gripping rotation knob (194). Simultaneously, the user retracts push arm (204) proximally toward its proximal position, for example via gripping element (228) arranged on push arm (204). Proximal retraction of push arm (204) causes racks (220) to rotate gears (230, 232, 236) in a second direction (e.g., counter-clockwise) opposite of the first direction described above, and thereby threadedly decouple ultrasonic transducer (208) from waveguide (196), as shown in FIG. 18B. Advantageously, one-way slip ratchet mechanism (240) is not configured to rotationally decouple third gear (236) from proximal transducer shaft (238) when the components of gear assembly (206) are rotated in the second direction during this retraction process. Accordingly, any suitable amount of retraction force may be applied to push arm (204) while maintaining transfer of decoupling torque to ultrasonic transducer (208) relative to waveguide (196).

C. Exemplary Rotation Lock Mechanism

Figure 19A:
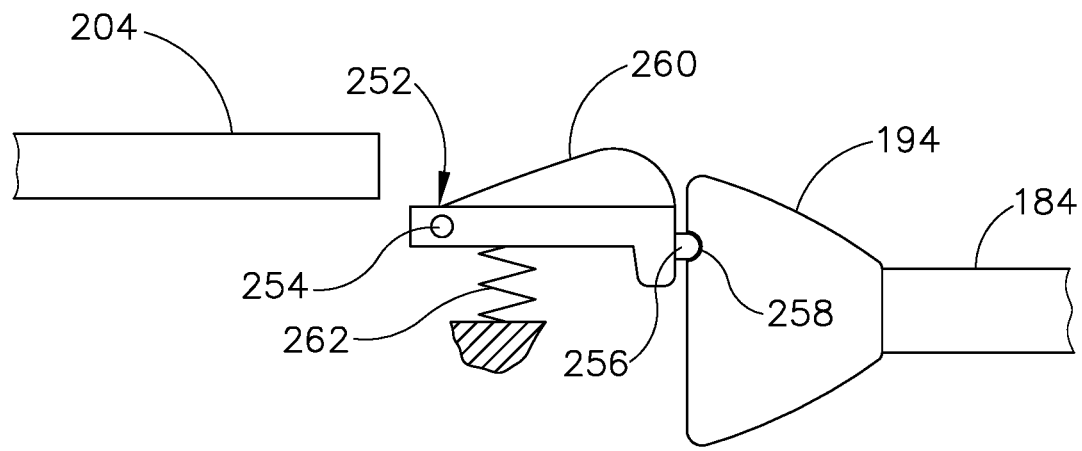
FIG. 19A depicts a schematic side sectional view of an exemplary rotation lock mechanism of the ultrasonic surgical instrument of FIG. 13, showing the rotation lock mechanism in a locked position in which rotation of the waveguide is prevented.
Figure 19B:
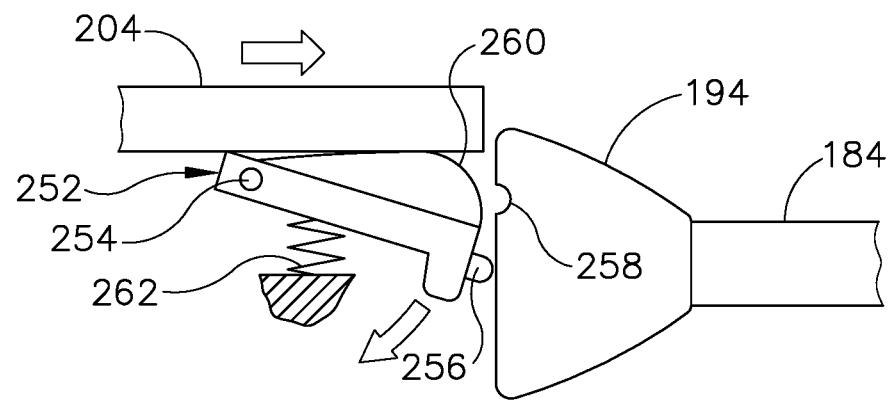
FIG. 19B depicts a schematic side sectional view of the rotation lock mechanism of FIG. 19A, showing the rotation lock mechanism in an unlocked position in which rotation of the waveguide is permitted.

FIGS. 19A and 19B show an exemplary rotation lock mechanism (250) configured to restrict rotation of waveguide (196) relative to handle assembly (182) during attachment and removal of proximal drive assembly (200) from handle assembly (182), thereby eliminating the need for a user to manually grip rotation knob (194) as described above. In the present example, rotation lock mechanism (250) is in the form of a knob lock mechanism having a lock member (252) configured to lockingly engage rotation knob (194) to prevent rotation of shaft assembly (184), including waveguide (196), relative to handle assembly (182). As described below, lock member (252) is movable between a locked position shown in FIG. 19A, and an unlocked position shown in FIG. 19B.

Lock member (252) includes an L-shaped lock body (186) having a proximal end that is pivotably coupled to body (186) of handle assembly (182) via a pivot pin (254). A distal end of lock body (186) includes a distally extending protrusion (256) configured to releasably engage a proximal portion of rotation knob (194). In the present example, rotation knob (194) includes a recess (258) formed in a proximal portion thereof. Recess (258) is configured to receive protrusion (256) when lock member (252) is in its locked position to thereby releasably, rotationally lock shaft assembly (184) relative to handle assembly (182), as shown in FIG. 19A. Lock member (252) further includes a sloped shoulder element (260) protruding from an upper surface of lock body (186) and tapering in a proximal direction. A resilient member (262) is positioned adjacent to lock member (252), for example beneath lock member (252), and is configured to bias lock member (252) into locking engagement with rotation knob (194) and thereby maintain rotation knob (194) and shaft assembly (184) in a default locked state, as shown in FIG. 19A. This default rotational locking of shaft assembly (184), including waveguide (196), enables ultrasonic transducer (208) to be threadedly engaged with waveguide (196) without requiring a user to manually restrain shaft assembly (184) by gripping rotation knob (194).

As shown in FIG. 19B, a distal end of push arm (204), shown schematically, is configured to engage sloped shoulder element (260) of lock member (252) when push arm (204) reaches its distal position in which ultrasonic transducer (1208) has been fully tightened relative to waveguide (196). For example, the distal end of push arm (204) may engage sloped shoulder element (260) once racks (220) have extended distally beyond and disengaged first and second gears (230, 232), as shown in FIG. 17C. It its distal position, a lower surface of push arm (204) forces lock member (252) to pivot downwardly such that protrusion (256) of lock member (252) disengages recess (258) of rotation knob (194). This disengagement enables rotation knob (194) and shaft assembly (184) to rotate freely relative to handle assembly (182) as needed, such as for performance of a surgical procedure. As shown in FIG. 19B, pivoting of lock member (252) to its unlocked position includes compressing resilient member (262). When push arm (204) is retracted proximally to remove proximal drive assembly (200) from handle assembly (182), as shown in FIG. 18A, push arm (204) disengages sloped shoulder element (260) of lock member (252). This enables resilient member (262) to expand and pivot lock member (252) upwardly back to its locked position shown in FIG. 19A in which shaft assembly (184) is restrained rotationally, thereby enabling threaded decoupling of ultrasonic transducer (208) from waveguide (196), as shown in FIG. 18B.

Alternative versions of rotation lock mechanism (250) may include various features other than, or in addition to, those described above. It will be understood that such features should be operable to restrict rotation of waveguide (196) relative to handle assembly (182) when proximal drive assembly (200) is being attached or removed from handle assembly (182), and permit rotation of waveguide (196) relative to handle assembly (182) when proximal drive assembly (200) is fully coupled to handle assembly (182). Further, while lock mechanism (250) is shown and described in connection with ultrasonic surgical instrument (180) described above, it will be understood that lock mechanism (250) and variations thereof may be incorporated into any of the exemplary ultrasonic surgical instruments described herein.

IV. EXEMPLARY ULTRASONIC SURGICAL INSTRUMENT AND EXTERNAL TORQUE WRENCH DEVICE HAVING KEYED FEATURES

Figure 20:
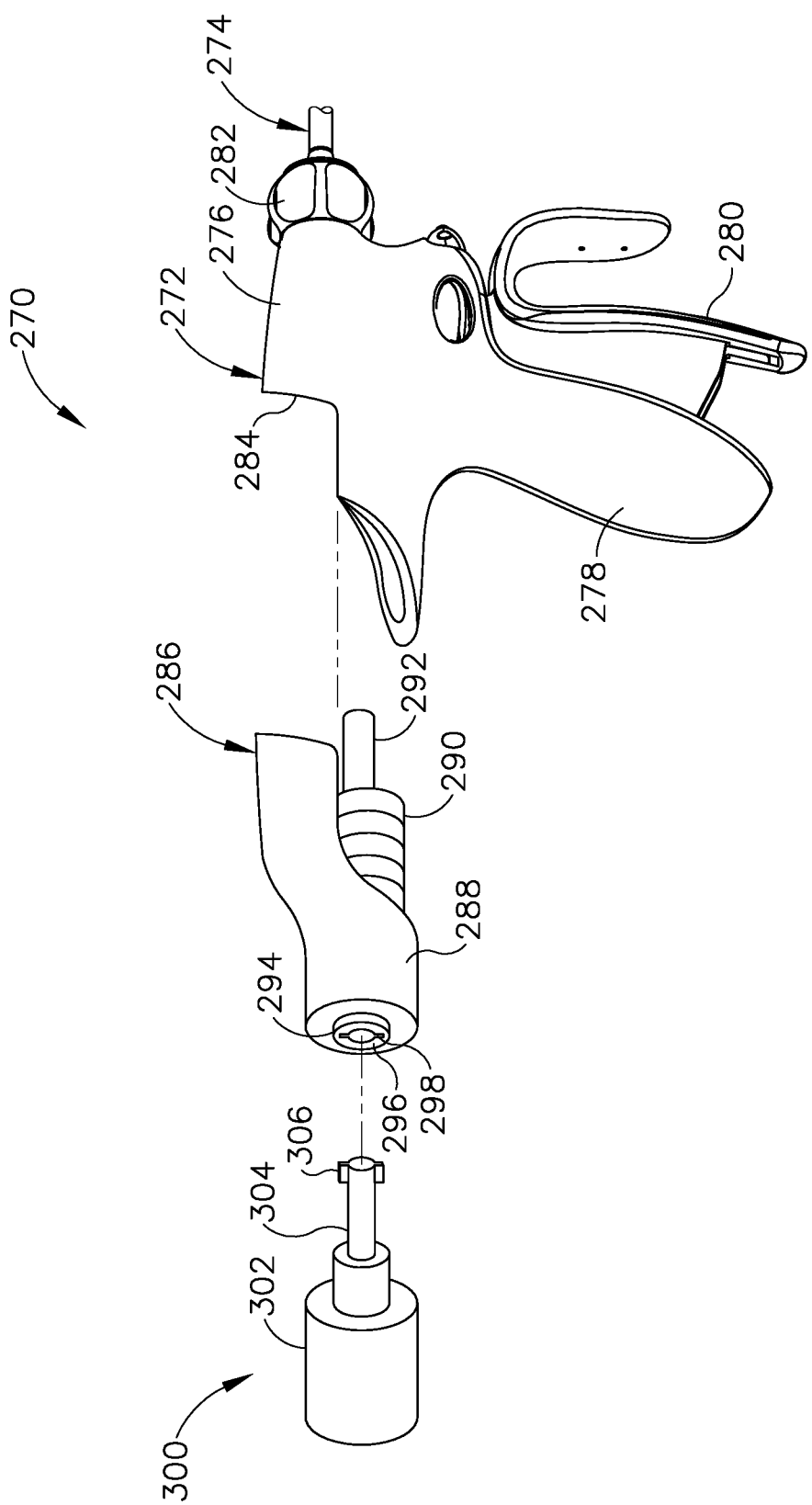
FIG. 20 depicts a partially disassembled perspective view of an exemplary ultrasonic surgical instrument having an ultrasonic transducer with a keyway, in combination with an exemplary, externally provided torque wrench device having a key element.

FIGS. 20 and 21 show an exemplary ultrasonic surgical instrument (270) in combination with a separately provided torque wrench device (300), defining a surgical instrument torque wrench system. Ultrasonic surgical instrument (270) includes a handle assembly (272), a shaft assembly (274) extending distally from handle assembly (272), and an end effector (not shown) arranged at a distal end of shaft assembly (274). Shaft assembly (274) and the end effector may be similar to shaft assembly (14) and end effector (16) described above.

Handle assembly (272) is similar to handle assembly (182) described above in that handle assembly (272) comprises a body (276) including a pistol grip (278), and may include control buttons (not shown) configured to be manipulated by a surgeon to control various aspects of tissue treatment energy delivered by surgical instrument (270). A trigger (280) is coupled to a lower portion of body (276) and is pivotable toward and away from pistol grip (278) to selectively actuate the end effector, which may be similar to end effector (16) described above. A rotation knob (282) is rotatably coupled to a distal end of body (276) and is rotatable with shaft assembly (274), including a waveguide thereof (not shown), relative to body (276) about a longitudinal axis defined by shaft assembly (274). A proximal end of body (276) includes a body opening (284) configured to receive a proximal drive assembly (286) of surgical instrument (270).

Proximal drive assembly (286) includes a frame (288) and an ultrasonic transducer (290) rotatably supported by frame (288). Ultrasonic transducer (290) is generally similar in structure and function to ultrasonic transducer (26) described above, including having an internally threaded distal end (292) configured to threadedly couple with an externally threaded proximal end of the waveguide of shaft assembly (274). For example, ultrasonic transducer (290) may threadedly couple to the waveguide of shaft assembly (274) in a manner similar to that described above in connection with FIG. 16B. Frame (288) has a proximal frame opening (294) formed in a proximal end thereof, which exposes a proximal transducer end (296) of ultrasonic transducer (290). As shown best in FIG. 21, proximal transducer end (296) includes a keyway (298) configured to receive a distal end of a torque wrench device (300), as described below.

Torque wrench device (300) is provided separately from ultrasonic surgical instrument (270) and includes a wrench body (302) and a wrench shaft (304) extending distally from wrench body (302). Wrench shaft (304) terminates at a distal tip having a key element (306) that is sized and shaped to be received within keyway (298) of ultrasonic transducer (290). More specifically, keyway (298) and key element (306) are formed with complementary shapes such that keyway (298) receives key element (306) therein only when wrench shaft (304) is aligned coaxially with ultrasonic transducer (290), and when key element (306) is positioned in one or more predetermined rotational orientations relative to keyway (298). Such cooperation between key element (306) and keyway (298) promotes optimal alignment and secure contact between torque wrench device (300) and ultrasonic transducer (290), thereby ensuring efficient transfer of torque from torque wrench device (300) to ultrasonic transducer (290). Advantageously, this enables a user to employ torque wrench device (300) to accurately apply a predetermined maximum torque to ultrasonic transducer (290) and its threaded coupling with the waveguide of shaft assembly (274).

The keyed configuration of surgical instrument (270) described above also ensures that only a torque wrench device configured to provide a specific maximum torque, such as torque wrench device (300), is usable with surgical instrument (270). This prevents inadvertent use of other torque wrench devices configured to provide other amounts of maximum torque, which could otherwise result in under-tightening or over-tightening of ultrasonic transducer (290) relative to the waveguide.

FIGS. 22A-22E show various exemplary cross-sectional shapes with which keyway (298) and/or key element (306) may be formed. FIG. 22A shows a first exemplary cross-sectional shape (310) having a central circular portion and first and second opposed rectangular portions extending outwardly from the central circular portion. FIG. 22B shows a second exemplary cross-sectional shape (312) defining a rectangle. FIG. 22C shows a third exemplary cross-sectional shape (314) defining a hexagon. FIG. 22D shows a fourth exemplary cross-sectional shape (316) defining a cross. FIG. 22E shows a fifth exemplary cross-sectional shape (318) having a central circular portion and four rectangular portions extending outwardly from the central circular portion at 90 degree increments. Those of ordinary skill in the art will appreciate that various other cross-sectional shapes may be used, or that a combination of shapes (310, 312, 314, 316, 318) described above may be used. For example, keyway (134) may be formed with first cross-sectional shape (310) and key element (306) may be formed with second cross-sectional shape (312).

Each exemplary shape (310, 312, 314, 316, 318) described above defines a corresponding quantity of rotational orientations in which key element (306) may be directed through keyway (298) (referred to below as "matching rotational orientations"), when each of key element (306) and keyway (298) is formed with the given shape (310, 312, 314, 316, 318). In particular, first shape (310) and second shape (312) each defines first and second matching rotational orientations. Third shape (314) defines six matching rotational orientations. Fourth shape (316) and fifth shape (318) each defines four matching rotational orientations.

In other versions of the surgical instrument torque wrench system shown in FIG. 20, torque wrench device (300) may be configured as a rigid tool with static components that omit any form of torque wrench mechanism, while ultrasonic surgical instrument (270) includes a torque wrench mechanism integrated within or coupled to proximal transducer end (296). Such a torque wrench mechanism may include features similar to those of any of the other exemplary torque wrench mechanisms described above, such as tabs (76, 150) and cam ramps (82, 152), for example. Such a configuration may be operated by first rotationally fixing shaft assembly (274) relative to handle assembly (272), for example by employing a rotation lock mechanism similar to lock mechanism (250) described above, or otherwise gripping rotation knob (282) manually. Key element (306) of device (300) may then be inserted distally into keyway (298) of ultrasonic transducer (290), and device (300) may be rotated to thereby rotate ultrasonic transducer (290) relative to waveguide of shaft assembly (274) and threadedly couple the components together. Upon reaching a predetermined maximum input torque applied by device (300), the torque wrench mechanism integrated within ultrasonic surgical instrument (270) would prevent further rotation of transducer (290) relative to the waveguide. Optionally, the integrated torque wrench mechanism may provide an audible, visible, and/or tactile indication to the user that the predetermined maximum torque has been reached.

While the teachings herein are disclosed in connection with ultrasonic surgical instruments, it will be appreciated that they may also be employed in connection with surgical instruments configured to provide a combination of ultrasonic and radio frequency (RF) energies. Examples of such instruments and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument comprising: (a) a body; (b) an ultrasonic transducer rotatably supported within the body and having a threaded distal end; (c) a shaft extending distally from the body; (d) a waveguide extending distally through the shaft and having a threaded proximal end configured to threadedly engage the threaded distal end of the ultrasonic transducer to define a threaded coupling therebetween; (e) an end effector arranged at a distal end of the shaft and including an ultrasonic blade coupled to the waveguide, wherein the ultrasonic transducer is configured to drive the waveguide and the ultrasonic blade with ultrasonic energy; and (f) an integrated torque wrench mechanism arranged within the body, wherein the integrated torque wrench mechanism comprises: (i) a first torque wrench member rotationally coupled with a proximal end of the ultrasonic transducer, and (ii) a second torque wrench member arranged proximally of the first torque wrench member, wherein the second torque wrench member is configured to selectively couple with the first torque wrench member such that the first and second torque wrench members frictionally engage one another to facilitate application of a predetermined maximum torque to the threaded coupling between the waveguide and the ultrasonic transducer, wherein the first and second torque wrench members are configured to automatically decouple from one another upon application of the predetermined maximum torque to the threaded coupling.

Example 2

The ultrasonic surgical instrument of Example 1, wherein a proximal end of the body includes a proximally facing opening configured to expose a user engageable portion of the second torque wrench member.

Example 3

The ultrasonic surgical instrument of Example 2, wherein the first torque wrench member, the second torque wrench member, and the user engageable portion are aligned coaxially with the ultrasonic transducer.

Example 4

The ultrasonic surgical instrument of any one or more of the previous Examples, wherein the second torque wrench member is translatable relative to the first torque wrench member between a proximal position and a distal position, wherein the second torque wrench member is configured to releasably couple with the first torque wrench member when in the distal position, wherein the second torque wrench member is configured to decouple from the first torque wrench member when in the proximal position.

Example 5

The ultrasonic surgical instrument of Example 4, wherein the second torque wrench member is resiliently biased toward the proximal position.

Example 6

The ultrasonic surgical instrument of any one or more of the previous Examples, wherein the first torque wrench member includes one of an opening or a projection and the second torque wrench member includes the other an opening or a projection, wherein the opening is configured to receive the projection to thereby releasably couple the first and second torque wrench member together.

Example 7

The ultrasonic surgical instrument of any one or more of the previous Examples, wherein the first torque wrench member includes one of a cam ramp or a follower element and the second torque wrench member includes the other of a cam ramp or a follower element, wherein the follower element is configured to frictionally engage the cam ramp when the first and second torque wrench members are coupled together, wherein the follower element is configured to move along the cam ramp during relative rotation between the first and second torque wrench members.

Example 8

The ultrasonic surgical instrument of Example 7, wherein the follower element and a peak of the cam ramp are configured to engage one another with a maximum friction force that limits relative rotation between the ultrasonic transducer and the waveguide, wherein the maximum friction force is configured to be overcome by a predetermined maximum torque applied to the threaded coupling between the waveguide and the ultrasonic transducer.

Example 9

The ultrasonic surgical instrument of any one or more of Examples 6 through 8, wherein the projection is configured to release from the opening upon application of the predetermined maximum torque to the threaded coupling.

Example 10

The ultrasonic surgical instrument of any one or more of Examples 7 through 9, wherein the first torque wrench member includes a pair of cam ramps and the second torque wrench member includes a pair of follower elements configured to frictionally engage the cam ramps.

Example 11

The ultrasonic surgical instrument of any one or more of Examples 7 through 10, wherein the follower element comprises a tab.

Example 12

The ultrasonic surgical instrument of any one or more of Examples 6 through 11, wherein the opening is configured to receive the projection with a snap-fit engagement, wherein the snap-fit engagement is configured to automatically release upon application of the predetermined maximum torque to the threaded coupling between the waveguide and the ultrasonic transducer.

Example 13

The ultrasonic surgical instrument of any one or more of Examples 6 through 11, wherein the projection defines a key element and the opening defines a keyway, wherein the key element is configured to pass through the keyway to thereby couple or decouple the first torque wrench member with the second torque wrench member when the key element is positioned in a predetermined rotational orientation relative to the keyway.

Example 14

The ultrasonic surgical instrument of any one or more of the preceding Examples, wherein each of the projection and the opening is formed with a non-circular transverse cross-section.

Example 15

The ultrasonic surgical instrument of any one or more of the preceding Examples, wherein the second torque wrench member is rotationally fixable relative to the body.

Example 16

An ultrasonic surgical instrument comprising: (a) a body; (b) an ultrasonic transducer rotatable relative to the body, wherein the ultrasonic transducer includes a threaded distal end, (c) a waveguide extending distally from the body and having a threaded proximal end configured to threadedly couple with the threaded distal end of the ultrasonic transducer to define a threaded coupling therebetween, wherein the ultrasonic transducer is configured to drive the waveguide with ultrasonic energy; (d) an integrated torque wrench mechanism comprising: (i) a translatable member, (ii) a rack coupled with the translatable member, and (iii) a gear rotationally coupled with the ultrasonic transducer and positioned to engage the rack, wherein the translatable member and the rack are translatable from a proximal position to a distal position to rotate the gear and thereby rotate the ultrasonic transducer into threaded engagement with the waveguide, wherein the integrated torque wrench mechanism is configured to limit transfer of torque to the ultrasonic transducer to thereby facilitate application of a predetermined maximum torque to the threaded coupling between the ultrasonic transducer and the waveguide.

Example 17

The ultrasonic surgical instrument of Example 16, wherein the rack is configured to decouple from the gear when the translatable member is in the distal position.

Example 18

The ultrasonic surgical instrument of any one or more of Examples 16 through 17, further comprising a ratchet mechanism configured to rotationally decouple the gear from the ultrasonic transducer upon application of the predetermined maximum torque to the threaded coupling between the ultrasonic transducer and the waveguide.

Example 19

The ultrasonic surgical instrument of any one or more of Examples 16 through 18, further comprising a rotation lock mechanism configured to inhibit rotation of the waveguide relative to the body while the ultrasonic transducer is being threadedly coupled with the waveguide.

Example 20

A surgical instrument torque wrench system comprising: (a) an ultrasonic surgical instrument comprising: (i) an instrument body, (ii) an ultrasonic transducer supported by the instrument body, wherein the ultrasonic transducer includes a keyway arranged on a proximal end thereof, (iii) a waveguide extending distally from the body and configured to threadedly couple with a distal end of the ultrasonic transducer to define a threaded coupling therebetween, and (iv) an ultrasonic blade extending distally from the waveguide; and (b) a torque wrench device comprising: (i) a wrench body, and (ii) a wrench shaft extending distally from the wrench body, wherein the wrench shaft includes a key element at a distal end thereof, wherein the key element is configured to engage the keyway to apply a torque to the threaded coupling between the waveguide and the ultrasonic transducer, wherein the key element and the keyway are formed with complementary shapes such that the keyway is configured to receive the key element only when the key element is positioned in one or more predetermined rotational orientations relative to the keyway.

VI. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCF™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument comprising:
   (a) a body;
   (b) an ultrasonic transducer rotatably supported within the body and having a threaded distal end;
   (c) a shaft extending distally from the body;
   (d) a waveguide extending distally through the shaft and having a threaded proximal end configured to threadedly engage the threaded distal end of the ultrasonic transducer to define a threaded coupling therebetween;
   (e) an end effector arranged at a distal end of the shaft and including an ultrasonic blade coupled to the waveguide, wherein the ultrasonic transducer is configured to drive the waveguide and the ultrasonic blade with ultrasonic energy; and
   (f) an integrated torque wrench mechanism arranged within the body, wherein the integrated torque wrench mechanism comprises:
      (i) a first torque wrench member rotationally coupled with a proximal end of the ultrasonic transducer, and
      (ii) a second torque wrench member arranged proximally of the first torque wrench member, wherein the second torque wrench member is translatable proximally and distally relative to the body,
      wherein the second torque wrench member is configured to selectively couple with the first torque wrench member such that the first and second torque wrench members frictionally engage one another to facilitate application of a predetermined maximum torque to the threaded coupling between the waveguide and the ultrasonic transducer,
      wherein the first and second torque wrench members are configured to automatically decouple from one another upon application of the predetermined maximum torque to the threaded coupling.

2. The ultrasonic surgical instrument of claim 1, wherein a proximal end of the body includes a proximally facing opening configured to expose a user engageable portion of the second torque wrench member.

3. The ultrasonic surgical instrument of claim 2, wherein the first torque wrench member, the second torque wrench member, and the user engageable portion are aligned coaxially with the ultrasonic transducer.

4. The ultrasonic surgical instrument of claim 1, wherein the second torque wrench member is translatable relative to the first torque wrench member between a proximal position and a distal position, wherein the second torque wrench member is configured to releasably couple with the first torque wrench member when in the distal position, wherein the second torque wrench member is configured to decouple from the first torque wrench member when in the proximal position.

5. The ultrasonic surgical instrument of claim 4, wherein the second torque wrench member is resiliently biased toward the proximal position.

6. The ultrasonic surgical instrument of claim 4, wherein the first torque wrench member includes one of an opening or a projection and the second torque wrench member includes the other of the opening or the projection, wherein the opening is configured to receive the projection to thereby releasably couple the first and second torque wrench member together.

7. The ultrasonic surgical instrument of claim 6, wherein the first torque wrench member includes one of a cam ramp or a follower element and the second torque wrench member includes the other of the cam ramp or the follower element, wherein the follower element is configured to frictionally engage the cam ramp when the first and second torque wrench members are coupled together, wherein the follower element is configured to move along the cam ramp during relative rotation between the first and second torque wrench members.

8. The ultrasonic surgical instrument of claim 7, wherein the follower element and a peak of the cam ramp are configured to engage one another with a maximum friction force that limits relative rotation between the ultrasonic transducer and the waveguide, wherein the maximum friction force is configured to be overcome by a predetermined maximum torque applied to the threaded coupling between the waveguide and the ultrasonic transducer.

9. The ultrasonic surgical instrument of claim 8, wherein the projection is configured to release from the opening upon application of the predetermined maximum torque to the threaded coupling.

10. The ultrasonic transducer of claim 7, wherein the first torque wrench member includes a pair of cam ramps and the second torque wrench member includes a pair of follower elements configured to frictionally engage the cam ramps.

11. The ultrasonic transducer of claim 7, wherein the follower element comprises a tab.

12. The ultrasonic surgical instrument of claim 6, wherein the opening is configured to receive the projection with a snap-fit engagement, wherein the snap-fit engagement is configured to automatically release upon application of the predetermined maximum torque to the threaded coupling between the waveguide and the ultrasonic transducer.

13. The ultrasonic surgical instrument of claim 6, wherein the projection defines a key element and the opening defines a keyway, wherein the key element is configured to pass through the keyway to thereby couple or decouple the first torque wrench member with the second torque wrench member when the key element is positioned in a predetermined rotational orientation relative to the keyway.

14. The ultrasonic surgical instrument of claim 6, wherein each of the projection and the opening is formed with a non-circular transverse cross-section.

15. The ultrasonic surgical instrument of claim 1, wherein the second torque wrench member is rotationally fixable relative to the body.

16. An ultrasonic surgical instrument comprising:
(a) a body;
(b) an ultrasonic transducer rotatably supported within the body and having a threaded distal end;
(c) a shaft extending distally from the body;
(d) a waveguide extending distally through the shaft and having a threaded proximal end configured to threadedly engage the threaded distal end of the ultrasonic transducer to define a threaded coupling therebetween;
(e) an end effector arranged at a distal end of the shaft and including an ultrasonic blade coupled to the waveguide, wherein the ultrasonic transducer is configured to drive the waveguide and the ultrasonic blade with ultrasonic energy; and
(f) an integrated torque wrench mechanism arranged within the body, wherein the integrated torque wrench mechanism includes:
(i) a distal torque wrench member coupled with a proximal end of the ultrasonic transducer, wherein a proximal face of the distal torque wrench member includes a first engagement feature, and
(ii) a proximal torque wrench member arranged proximally of the distal torque wrench member, wherein a distal face of the proximal torque wrench member includes a second engagement feature,
wherein the first engagement feature of the distal torque wrench member is configured to frictionally engage the second engagement feature of the proximal torque wrench member to facilitate application of a predetermined maximum torque to the threaded coupling between the waveguide and the ultrasonic transducer,
wherein the first and second engagement features are configured to automatically disengage one another upon application of the predetermined maximum torque to the threaded coupling.

17. The ultrasonic surgical instrument of claim 16, wherein the first engagement feature includes one of a cam ramp or a protrusion, wherein the second engagement feature includes the other of the cam ramp or the protrusion.

18. An ultrasonic surgical instrument comprising:
(a) a body;
(b) an ultrasonic transducer rotatably supported within the body and having a threaded distal end, wherein the ultrasonic transducer defines a longitudinal axis;
(c) a shaft extending distally from the body;
(d) a waveguide extending distally through the shaft and having a threaded proximal end configured to threadedly engage the threaded distal end of the ultrasonic transducer to define a threaded coupling therebetween;
(e) an end effector arranged at a distal end of the shaft and including an ultrasonic blade coupled to the waveguide, wherein the ultrasonic transducer is configured to drive the waveguide and the ultrasonic blade with ultrasonic energy; and
(f) an integrated torque wrench mechanism arranged within the body, wherein the integrated torque wrench mechanism includes:
(i) a distal torque wrench member coupled with a proximal end of the ultrasonic transducer and having a first coupling feature disposed along the longitudinal axis, and
(ii) a proximal torque wrench member arranged proximally of the distal torque wrench member and having a second coupling feature disposed along the longitudinal axis,
wherein the first and second coupling features are configured to engage to releasably couple the distal and proximal torque wrench members together,
wherein the distal and proximal torque wrench members are configured to frictionally engage one another to facilitate application of a predetermined maximum torque to the threaded coupling between the waveguide and the ultrasonic transducer, wherein the first and second coupling features are configured to automatically decouple upon application of the predetermined maximum torque to the threaded coupling.

19. The ultrasonic surgical instrument of claim 18, wherein the first coupling feature includes one of a protrusion or an opening, wherein the second coupling feature includes the other of the protrusion or the opening, wherein the opening is configured to receive the protrusion therein.

* * * * *